United States Patent
Ikuma et al.

(10) Patent No.: US 8,204,576 B2
(45) Date of Patent: Jun. 19, 2012

(54) MEDICAL GUIDING SYSTEM

(75) Inventors: Soichi Ikuma, Hachioji (JP); Tomonao Kawashima, Hachioji (JP); Masahiko Komuro, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 902 days.

(21) Appl. No.: 12/132,973

(22) Filed: Jun. 4, 2008

(65) Prior Publication Data

US 2008/0306379 A1 Dec. 11, 2008

(30) Foreign Application Priority Data

Jun. 6, 2007 (JP) .................................. 2007-150923

(51) Int. Cl.
*A61B 5/05* (2006.01)
(52) U.S. Cl. ....................................................... 600/424
(58) Field of Classification Search ........................ None
See application file for complete search history.

(56) References Cited

U.S. PATENT DOCUMENTS

| | | | |
|---|---|---|---|
| 6,618,612 B1 | 9/2003 | Acker et al. | |
| 7,477,763 B2* | 1/2009 | Willis et al. | 382/128 |
| 7,736,316 B2* | 6/2010 | Kawashima et al. | 600/443 |
| 7,774,045 B2* | 8/2010 | Ikuma et al. | 600/424 |
| 7,804,991 B2* | 9/2010 | Abovitz et al. | 382/128 |
| 7,824,328 B2* | 11/2010 | Gattani et al. | 600/117 |
| 2003/0231789 A1* | 12/2003 | Willis et al. | 382/128 |
| 2004/0171924 A1 | 9/2004 | Mire et al. | |
| 2005/0085717 A1* | 4/2005 | Shahidi | 600/424 |
| 2005/0085718 A1* | 4/2005 | Shahidi | 600/424 |
| 2006/0036162 A1* | 2/2006 | Shahidi et al. | 600/424 |
| 2007/0078334 A1 | 4/2007 | Scully et al. | |
| 2007/0078343 A1* | 4/2007 | Kawashima et al. | 600/443 |
| 2007/0167769 A1* | 7/2007 | Ikuma et al. | 600/437 |
| 2007/0239009 A1* | 10/2007 | Kawashima et al. | 600/437 |

(Continued)

FOREIGN PATENT DOCUMENTS

| | | |
|---|---|---|
| JP | 2000-506259 A | 5/2000 |
| JP | 2006-149481 | 6/2006 |

OTHER PUBLICATIONS

Fitzpatrick, Michael J., et al., "Predicting Error in Rigid-Body Point-Based Registration", IEEE Transactions on Medical Imaging, vol. 17, No. 5, Oct. 1998, pp. 694-702.

(Continued)

*Primary Examiner* — Long V. Le
*Assistant Examiner* — Angela M Hoffa
(74) *Attorney, Agent, or Firm* — Scully, Scott, Murphy & Presser, P.C.

(57) ABSTRACT

A medical guiding system of the invention includes: a detection portion for detecting a position and an orientation of a medical instrument and positions of feature points of a subject; a storage portion for storing reference image data having positional information on an organ of a human body; and a guide image creation portion for creating a guide image indicating the position of the medical instrument with respect to the subject from the reference image data. The guide image creation portion calculates the position of the medical instrument with respect to the subject, based on the position and the orientation of the medical instrument and the positions of feature points of the subject which are detected by the detection portion, and creates a guide image by correcting the calculated position of the medical instrument, using the positions of the feature points.

5 Claims, 16 Drawing Sheets

| SCANNING REGION | TRANSLATION CORRECTION | TRANSLATION CORRECTION FEATURE POINT D | SCALE SIZE CORRECTION | FIRST SCALE SIZE CORRECTION FEATURE POINT E | SECOND SCALE SIZE CORRECTION FEATURE POINT F |
|---|---|---|---|---|---|
| STOMACH | ON | CARDIA | ON | DUODENAL PAPILLA | CARDIA |
| DUODENAL BULB | ON | PYLORUS | ON | DUODENAL PAPILLA | CARDIA |
| DUODENAL DESCENDING LIMB | ON | DUODENAL PAPILLA | OFF | | |

102

U.S. PATENT DOCUMENTS

| | | | |
|---|---|---|---|
| 2007/0299336 A1* | 12/2007 | Ikuma et al. | 600/424 |
| 2008/0004529 A1* | 1/2008 | Kawashima et al. | 600/443 |
| 2008/0269596 A1* | 10/2008 | Revie et al. | 600/424 |
| 2008/0281189 A1* | 11/2008 | Komuro et al. | 600/424 |
| 2009/0036775 A1* | 2/2009 | Ikuma et al. | 600/443 |
| 2009/0175518 A1* | 7/2009 | Ikuma et al. | 382/128 |
| 2010/0280365 A1* | 11/2010 | Higgins et al. | 600/424 |

OTHER PUBLICATIONS

Extended European Search Report, dated Sep. 21, 2011, in counterpart European Patent Application No. EP 08010054.8.

Japanese Office Action dated Apr. 3, 2012 issued in counterpart Japanese Patent Application No. 2007-150923.

* cited by examiner

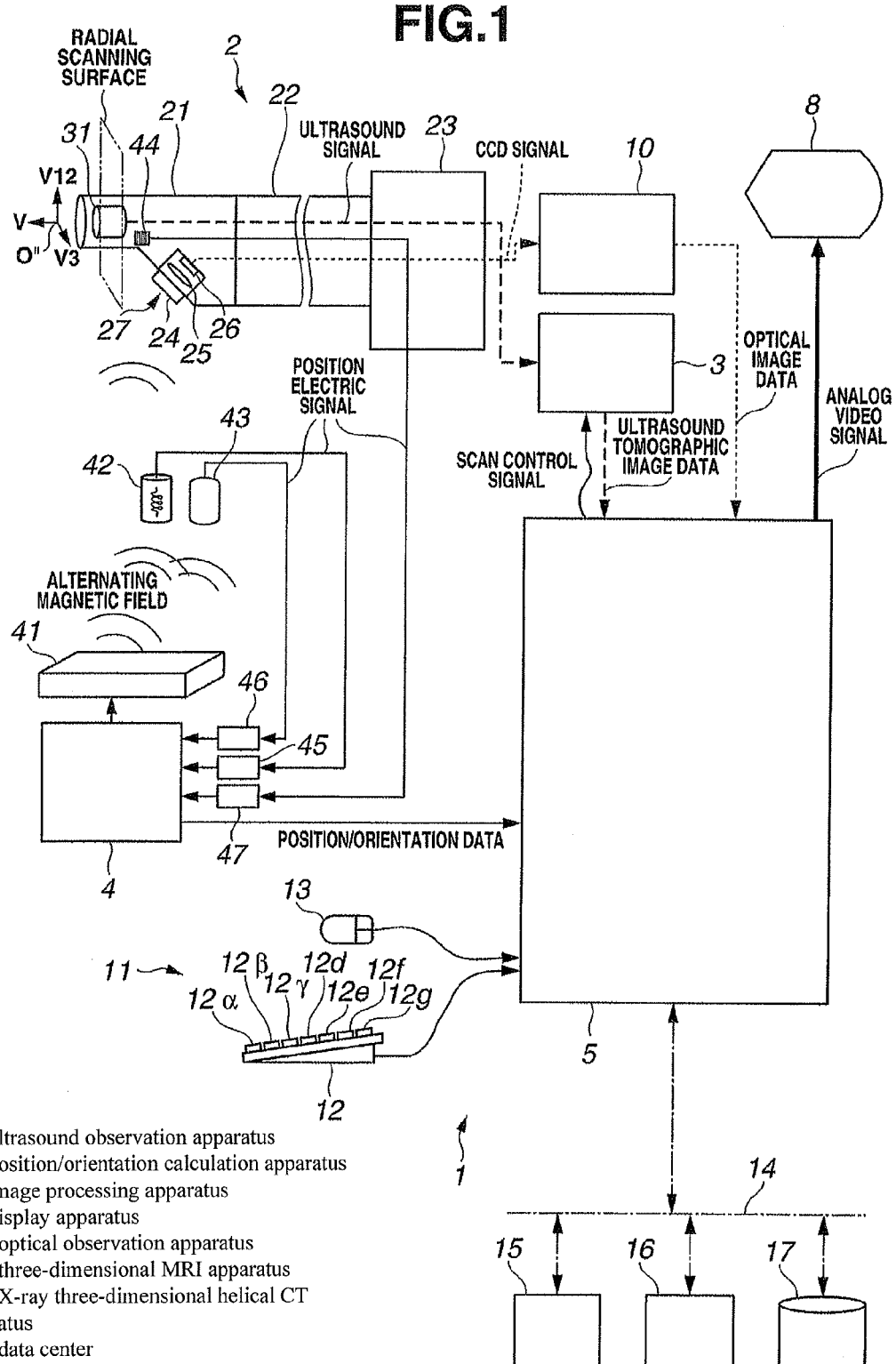

FIG.1

3... ultrasound observation apparatus
4... position/orientation calculation apparatus
5... image processing apparatus
8... display apparatus
10... optical observation apparatus
15... three-dimensional MRI apparatus
16... X-ray three-dimensional helical CT apparatus
17... data center
23... operation portion
41... transmission antenna
45... A/D conversion apparatus
46... A/D conversion apparatus
47... A/D conversion apparatus 3... ultrasound observation apparatus
4... position/orientation calculation apparatus
8... display apparatus
10... optical observation apparatus
51... communication circuit
52... reference image storage portion
53... interpolation circuit
53a... interpolation memory
54... three-dimensional human body image creation circuit
60... control circuit
61... matching circuit
62... image index creation circuit
63... synthesis circuit
63a...voxel space in synthesis memory
64... rotational transformation circuit
65... three-dimensional guide image creation circuit
66... three-dimensional guide image creation circuit
67... mixing circuit
68... display circuit
69... switch
101... feature point list
102... correction condition table
GRD... group of reference image data

FIG.3

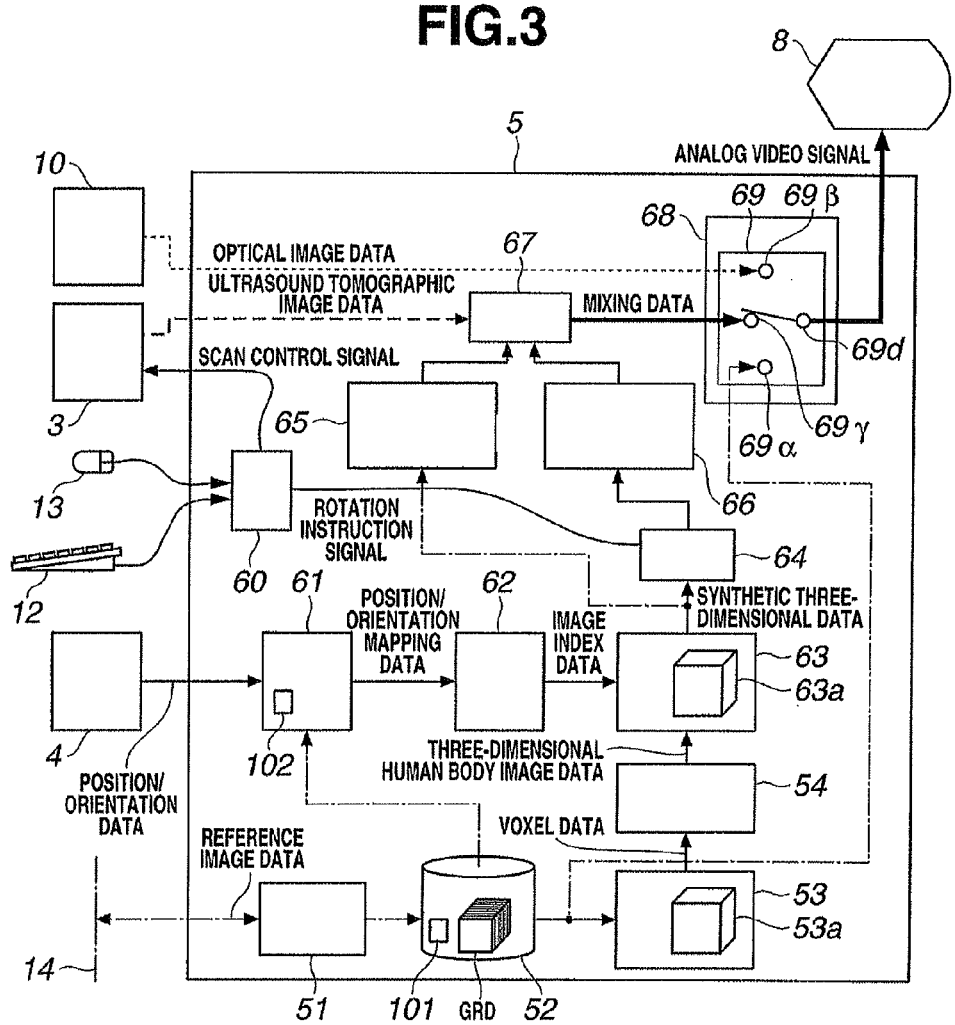

| No. | FEATURE POINT |
|---|---|
| 1 | XIPHOID PROCESS |
| 2 | LEFT ANTERIOR SUPERIOR ILIAC SPINE |
| 3 | RIGHT ANTERIOR SUPERIOR ILIAC SPINE |
| 4 | SPINOUS PROCESS OF VERTEBRAL BODY |
| 5 | DUODENAL PAPILLA |
| 6 | CARDIA |
| 7 | PYLORUS |

FIG.6
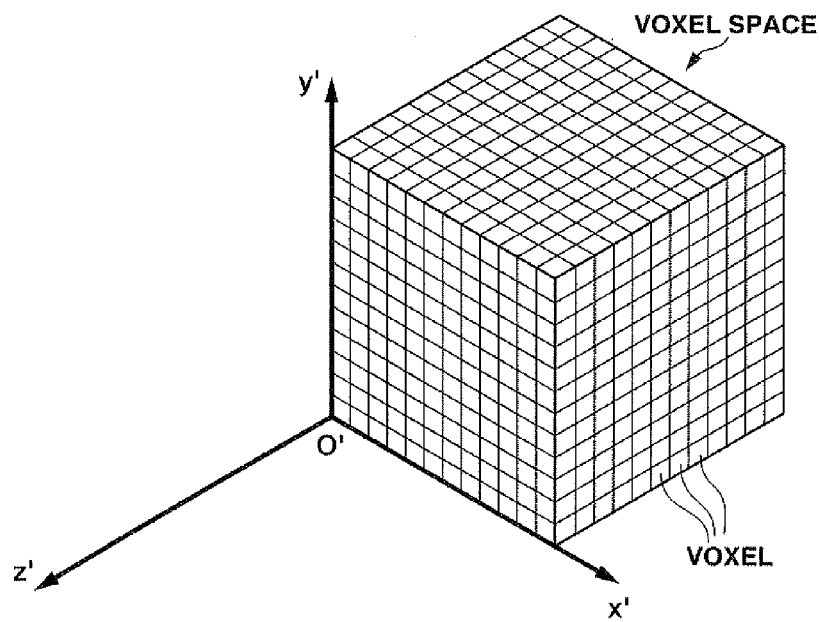
FIG.7
| SCANNING REGION | TRANSLATION CORRECTION | TRANSLATION CORRECTION FEATURE POINT D | SCALE SIZE CORRECTION | FIRST SCALE SIZE CORRECTION FEATURE POINT E | SECOND SCALE SIZE CORRECTION FEATURE POINT F |
|---|---|---|---|---|---|
| STOMACH | ON | CARDIA | ON | DUODENAL PAPILLA | CARDIA |
| DUODENAL BULB | ON | PYLORUS | ON | DUODENAL PAPILLA | CARDIA |
| DUODENAL DESCENDING LIMB | ON | DUODENAL PAPILLA | OFF | — | — |
FIG.8
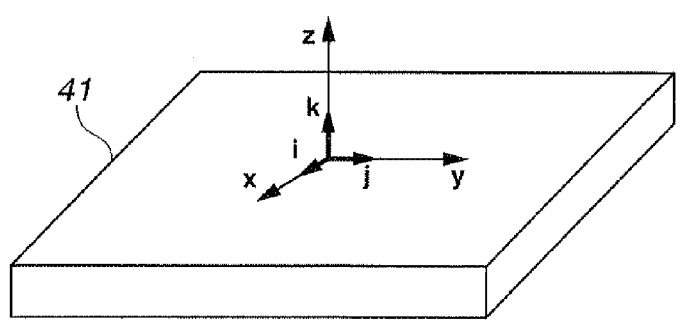

FIG.9
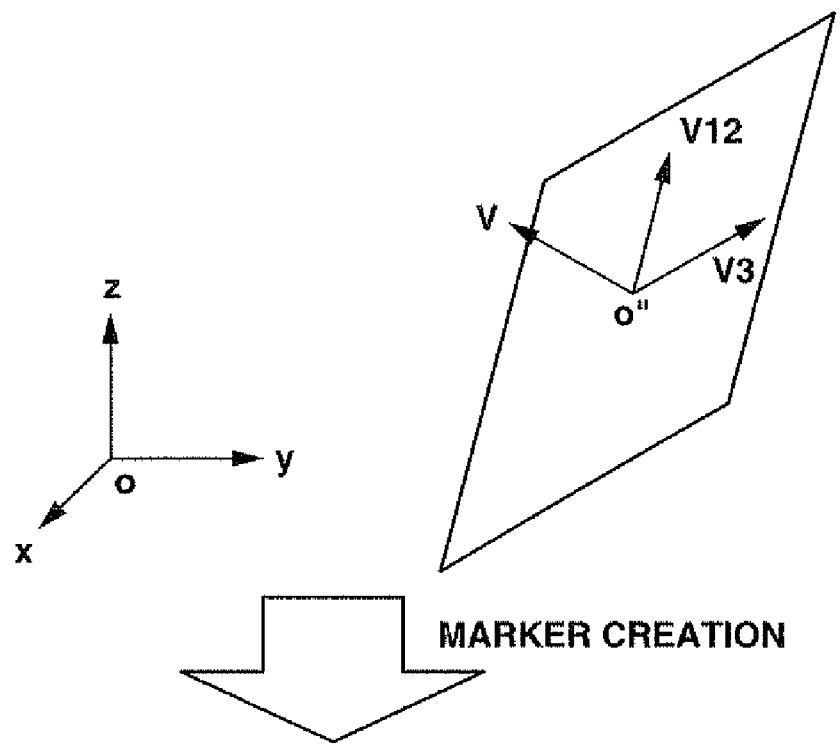
MARKER CREATION
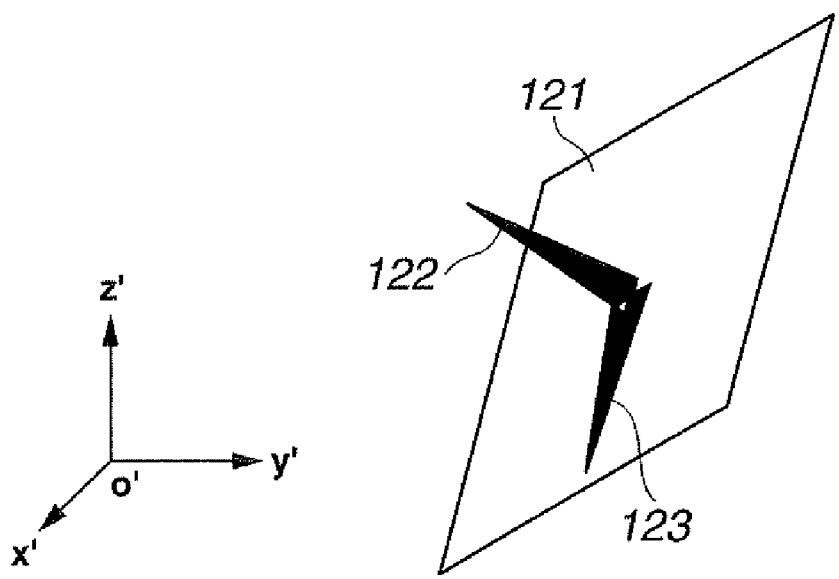

FOOT SIDE ← 111, 112, 113 → HEAD SIDE

FOOT SIDE ← 111, 121, 123, 122, 112, 113 → HEAD SIDE

81

FIG.20
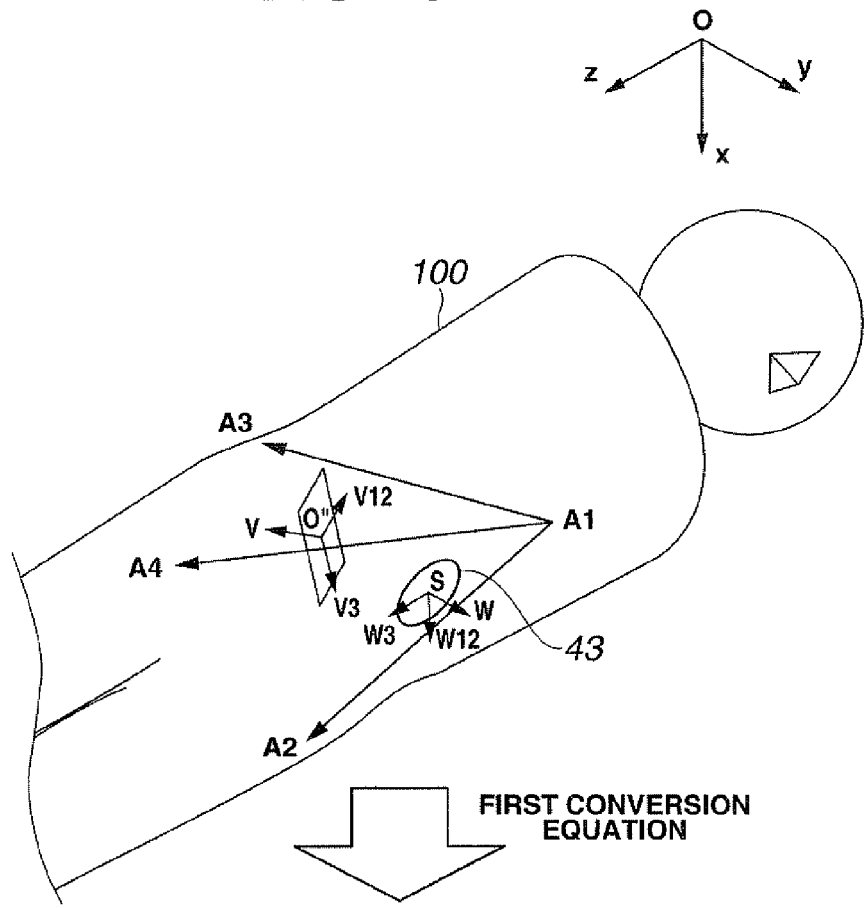
FIRST CONVERSION EQUATION
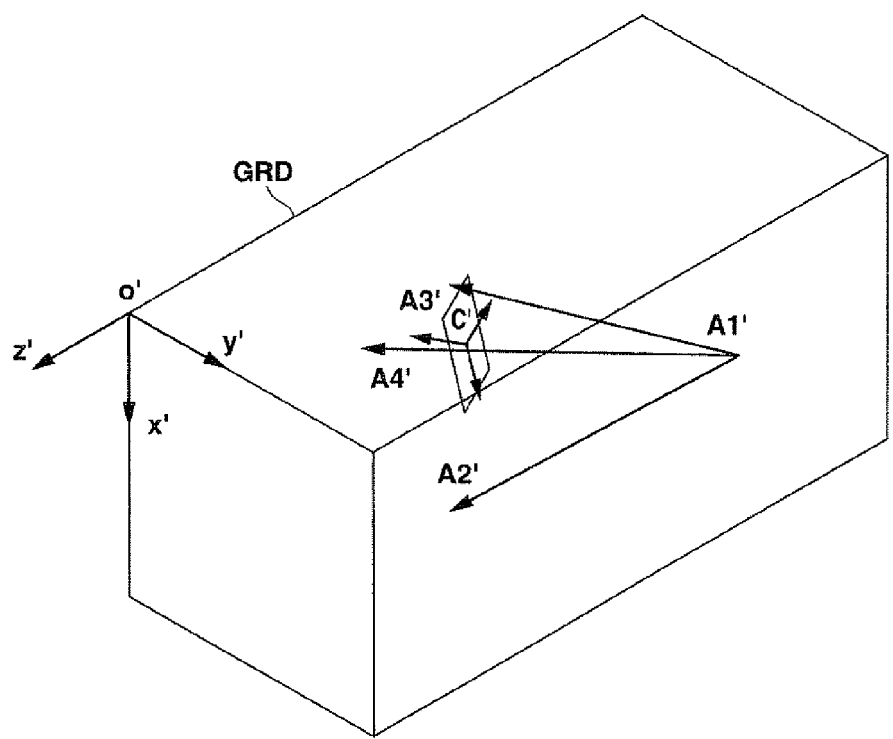

MEDICAL GUIDING SYSTEM

CROSS REFERENCE TO RELATED APPLICATION

This application claims benefit of Japanese Application No. 2007-150923 filled in Japan on Jun. 6, 2007, the contents of which are incorporated by this reference.

BACKGROUND OF THE INVENTION

1. Field of the Invention

The present invention relates to a medical guiding system showing a position of a medical instrument in reference image data having anatomical positional information of at least one of a viscus and an organ of a human body and guiding the medical instrument.

2. Description of Related Art

There has been conventionally well-known a medical instrument as typified by an endoscope, an ultrasound endoscope, a small-diameter ultrasound probe or the like, which is introduced into gastrointestinal tract, biliopancreatic duct, blood vessels, etc. in the body, to be used for diagnosis, treatment, operation and the like. The endoscope includes a bronchoscope, a gastrointestinal endoscope, a laparoscope, and the like. Also, there is well-known a medical instrument to diagnose and treat the viscera and organs from body surface, as typified by an ultrasound diagnostic apparatus.

When performing diagnosis or operation using the medical instrument with respect to a living body, an operator performs diagnosis and surgery assuming anatomical position under current observation, while previously taking into account known anatomical positional relationships of the organs or the tissues in a living body.

In order to assist such diagnosis and surgery, there have been proposed techniques for displaying a guide image guiding a current anatomical position of the medical instrument at the time of diagnosis and surgery, through synthesis based on a CT image or an MRI image obtained in advance.

As a medical guiding apparatus, Japanese Patent Application Laid-Open No. 2006-149481, for example, describes a technique for detecting a distal end position of an ultrasound endoscope to construct a guide image corresponding to an anatomical position of the ultrasound endoscope based on an anatomical image data and display the constructed guide image.

In the technique disclosed in Japanese Patent Application Laid-Open No. 2006-149481, sample point position detection means for detecting a position of a sample point of a living body is provided and the position of the sample point detected by the sample point position detection means is checked against a position of a feature point on reference image data retained in image information retention means to create a guide image. In addition, body position detection means for detecting a position or an orientation of a living body is mounted to a subject. Based on the position or orientation of the subject detected by the body position detection means, the position of the sample point detected by the sample point position detection means is corrected, and thereby the guide image is created while correcting a variation of body position of the subject.

SUMMARY OF THE INVENTION

A medical guiding system according to the present invention includes: a detection portion for detecting at least one of a position and an orientation of a medical instrument and at least one of positions and orientations of a plurality of feature points of a subject; a storage portion for storing reference image data having anatomical positional information on at least one of a viscus and an organ of a human body; and a guide image creation portion for creating a guide image indicating a position of the medical instrument or an observation position by the medical instrument with respect to the subject based on the reference image data, in which the guide image creation portion calculates the position of the medical instrument or the observation position by the medical instrument with respect to the subject, based on at least one of the position and the orientation of the medical instrument and at least one of the positions and the orientations of the feature points of the subject which are detected by the detection portion, and creates a guide image by correcting the calculated position of the medical instrument or the calculated observation position by the medical instrument, using the positions of the plurality of feature points.

The above and other objects, features and advantages of the invention will become more clearly understood from the following description referring to the accompanying drawings.

BRIEF DESCRIPTION OF THE DRAWINGS

FIG. 1 is a diagram showing a configuration of a medical guiding system of a first embodiment.

FIG. 3 is a block diagram showing a configuration of an image processing apparatus.

FIG. 6 is a diagram showing a configuration of a voxel space.

FIG. 7 is a table showing a correction condition table.

FIG. 8 is a diagram showing an origin and an orthogonal coordinate system and the like defined on a transmission antenna.

FIG. 9 is a diagram showing a situation of an ultrasound tomographic image marker.

FIG. 20 is a diagram for describing a first mapping.

DETAILED DESCRIPTION OF PREFERRED EMBODIMENTS

Figure 2:
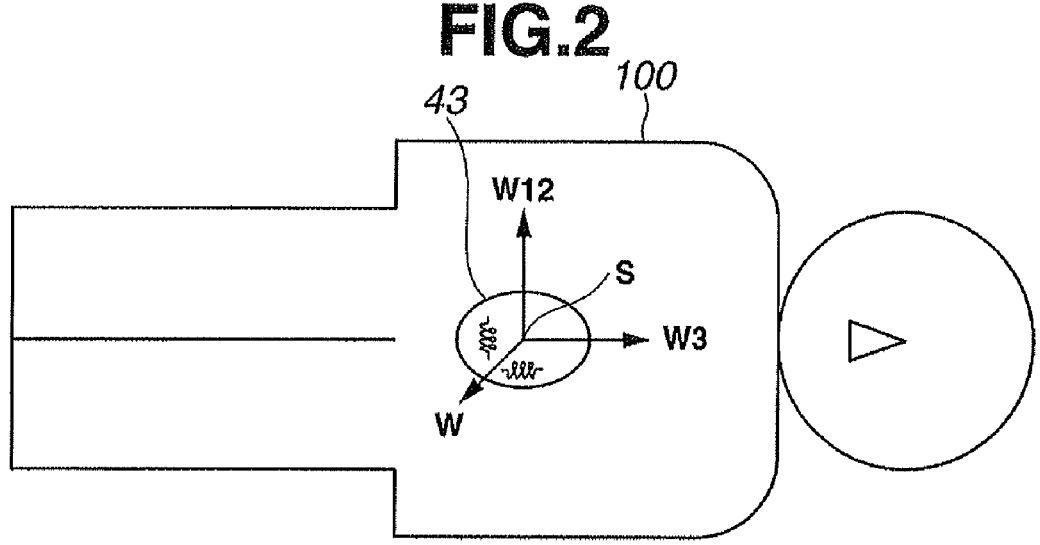
FIG. 2 is a diagram showing a configuration of a posture detection coil.

Hereinafter, the present invention is described based on embodiments shown in the drawings. Note that the present invention is not limited to the shape, the size ratio, or disposing position of each of the components and the like shown in the drawings.

(First Embodiment)

Figures 4, 5:
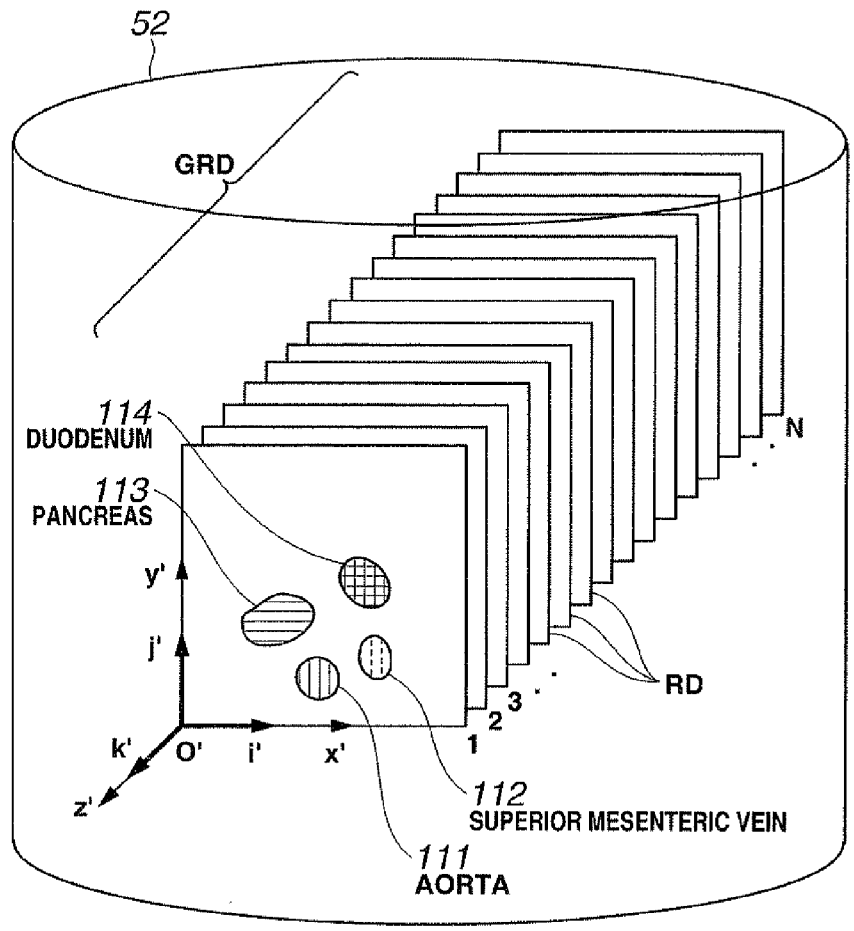
FIG. 4 is a diagram conceptually showing reference image data stored in a reference image storage portion.
FIG. 5 is a table showing a feature point list.
Figure 10:
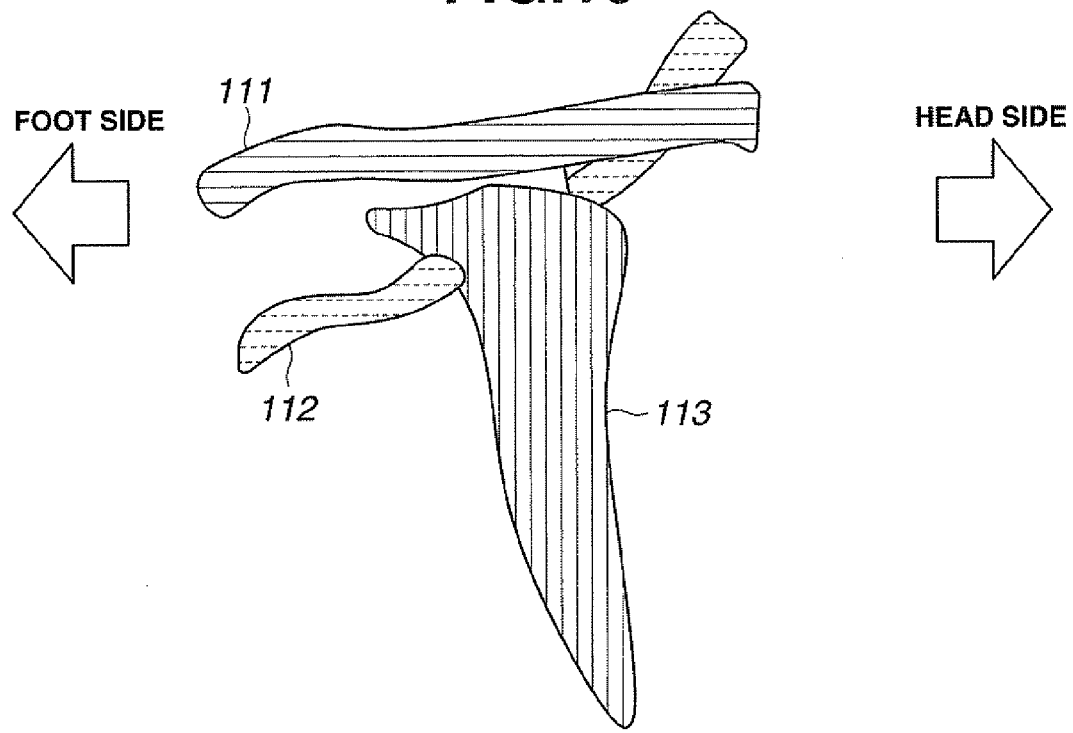
FIG. 10 is a diagram showing three-dimensional human body image data.
Figure 11:
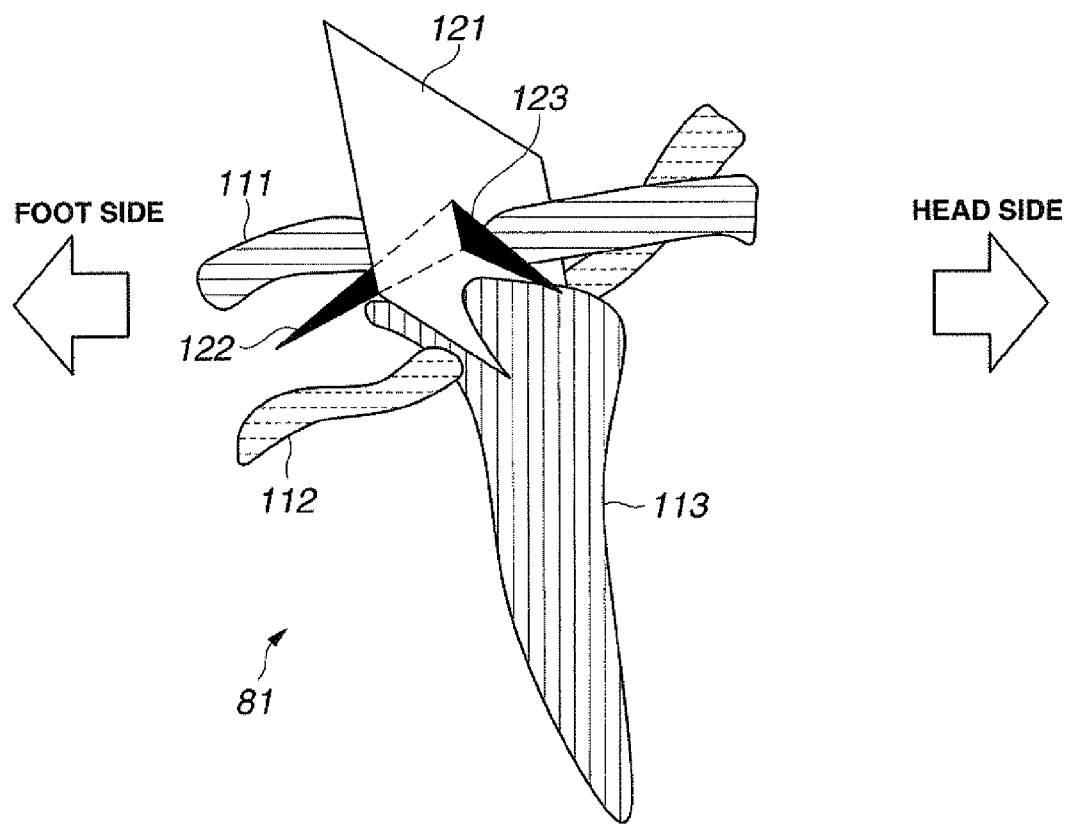
FIG. 11 is a diagram showing three-dimensional guide image data.
Figure 12:
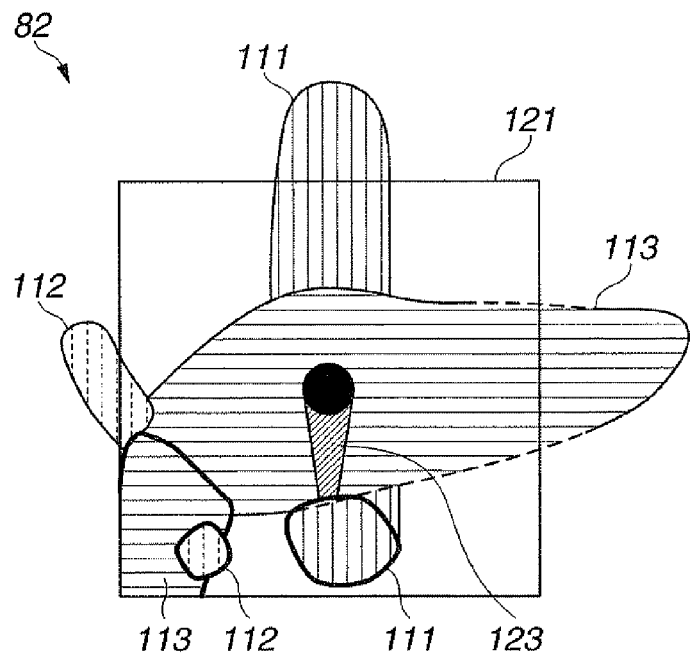
FIG. 12 is a diagram showing three-dimensional guide image data.
Figure 13:
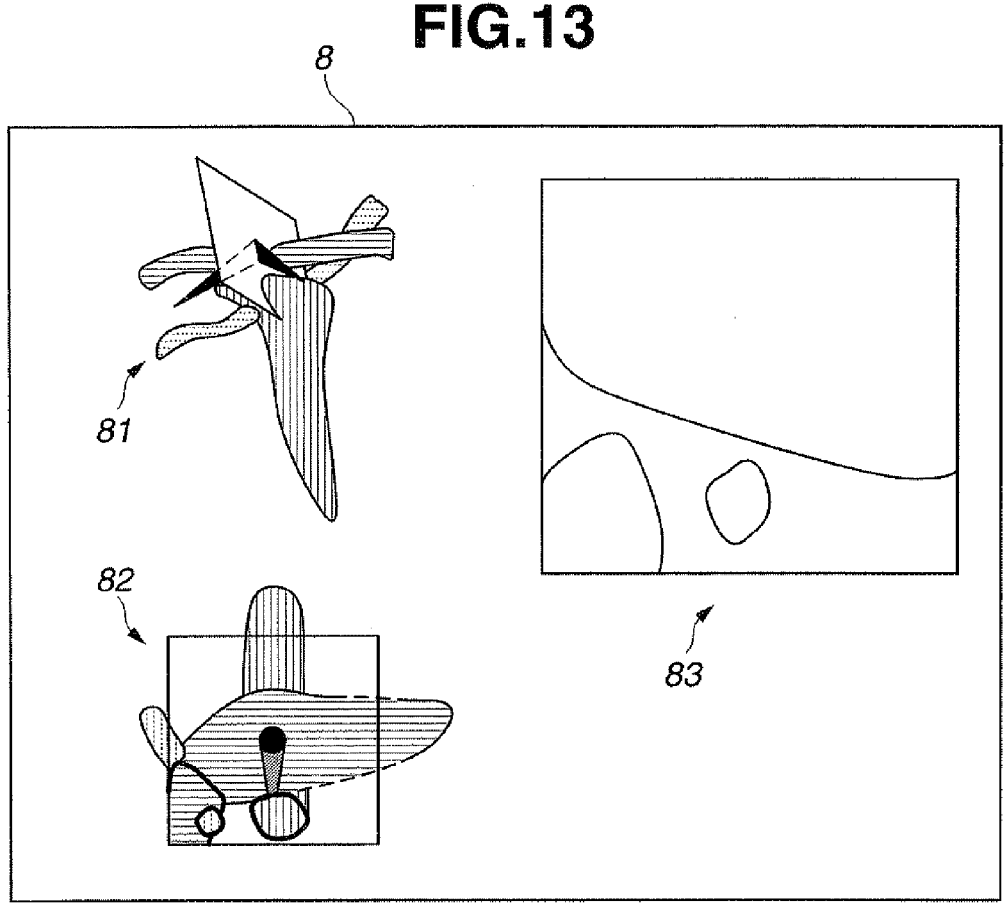
FIG. 13 is a diagram showing a three-dimensional guide image displayed on a display apparatus.

Hereinafter, a first embodiment of the present invention is described with reference to the drawings. FIG. 1 is a block diagram showing a configuration of a medical guiding system. FIG. 2 is a diagram showing a configuration of a posture detection coil. FIG. 3 is a block diagram showing a configuration of an image processing apparatus. FIG. 4 is a diagram conceptually showing reference image data stored in a reference image storage portion. FIG. 5 is a table showing a feature point list. FIG. 6 is a diagram showing a configuration of a voxel space. FIG. 7 is a table showing a correction condition table. FIG. 8 is a diagram showing an origin and an orthogonal coordinate system and the like defined on a transmission antenna. FIG. 9 is a diagram showing a situation of an ultrasound tomographic image marker. FIG. 10 is a diagram showing three-dimensional human body image data. FIGS. 11 and 12 are diagrams showing three-dimensional guide image data. FIG. 13 is a diagram showing a three-dimensional guide image displayed on a display apparatus.

A medical guiding system 1 according to the present embodiment serves as a system for performing guiding to assist introduction of an ultrasound endoscope 2 as a medical instrument into a body. The medical guiding system I according to the present embodiment includes the ultrasound endoscope 2, an ultrasound observation apparatus 3, a position/orientation calculation apparatus 4, an image processing apparatus 5, a display apparatus 8, an optical observation apparatus 10, and an input device 11, and each of the apparatuses are connected by wired or wireless communication means.

In addition, the medical guiding system 1 is connected to a network 14 using an optical fiber, an electrical cable, or wireless communication and the like, which is provided outside of the medical guiding system 1. The network 14 is connected with an X-ray three-dimensional helical CT apparatus (X-ray 3-dimensional computed tomography system) 16, a three-dimensional MRI apparatus (3-dimensional magnetic resonance imaging system) 15, and an external storage apparatus 17. The medical guiding system 1 is capable of transmitting and receiving data with the three-dimensional MRI apparatus 15, the X-ray three-dimensional helical CT apparatus 16, and the external storage apparatus 17, via the network 14.

The ultrasound endoscope 2 as a medical instrument includes: a rigid portion 21 configured of a rigid material such as stainless steel and disposed at a distal end of an insertion portion to be used inserted into a body inside such as an esophagus, a stomach, a duodenum, and the like; a long flexible portion 22 configured of a flexible material and disposed on a proximal end side of the rigid portion 21; and an operation portion 23 configured of a rigid material and disposed on a proximal end side of the flexible portion 22. An operator grasps the operation portion 23 to operate the ultrasound endoscope 2. In addition, the ultrasound endoscope 2 is electrically connected to the ultrasound observation apparatus 3, the optical observation apparatus 10, and the position/orientation calculation apparatus 4 via a connecting connector not shown.

The rigid portion 21 includes an image pickup apparatus 27, an ultrasound transducer array 31, and an image position/orientation detection coil 44. The image pickup apparatus 27 includes a CCD (Charge Coupled Device) 26 as an image pickup device, a lens 25 for forming an image of a subject on a light-receiving surface of the CCD 26, and the like, and serves as an apparatus for optically picking up an image of inside of the body through an optical observation window 24 made of glass. The rigid portion 21 is provided with an illumination apparatus not shown for irradiating illumination light in a field of view direction of the image pickup apparatus 27. The image pickup apparatus 27 obtains an optical image of the body inside illuminated by the illumination apparatus to output the obtained image as a CCD signal to the optical observation apparatus 10.

The ultrasound transducer array 31 is a so-called electronic radial scan ultrasound transducer array and configured of a plurality of ultrasound transducers annularly disposed around an insertion axis along an insertion direction of the rigid portion 21 into the body. The ultrasound transducer array 31 transmits and receives an ultrasound beam while scanning the ultrasound beam in a radiation direction on a plane orthogonal to the insertion axis, to obtain an echo signal required for obtaining an ultrasound tomographic image and outputs the obtained echo signal to the ultrasound observation apparatus 3.

The ultrasound transducer array 31 is electrically connected to the ultrasound observation apparatus 3. The ultrasound observation apparatus 3 controls intensity, angle, focus, and the like of the ultrasound beam transmitted by the ultrasound transducer array 31, to generate ultrasound tomographic image data on a scanning surface from the echo signal obtained by the ultrasound transducer array 31 and outputs the generated ultrasound tomographic image data.

Note that, hereinafter, the surface to be scanned by the ultrasound transducer array 31 is called as a scanning surface. In addition, orthonormal bases (unit vectors of the respective directions) V, V3, and V12 fixed to the rigid portion 21 are defined as shown in FIG. 1. That is, the base vector V is defined to be parallel to an insertion axis direction of the rigid portion 21, in other words, a normal direction vector of the scanning surface, and in a case where a predetermined scan direction of the ultrasound transducer array 31 is assumed to be the twelve o'clock direction, the base vector to orient in the three o'clock direction is defined as V3, and the base vector to orient in the twelve o'clock direction is defined as V12. Note that, though vectors are normally described in bold italics, the vectors are denoted in normal alphanumeric characters in the present embodiment.

The image position/orientation detection coil 44 is disposed in the rigid portion 21 so as to be located in the vicinity of the center of the circular ultrasound transducer array 31 with the positional relationship with respect to the ultrasound transducer array 31 fixed. The image position/orientation detection coil 44 includes integrally formed two coils respectively wound around the axes parallel to the base vectors V and V3.

The positional relationship between the optical observation window 24 and the image position/orientation detection coil 44 is also fixed, so that the position of the optical observation window 24 can be calculated by moving the coordinates by predetermined values e, f, and g in the respective directions of the orthonormal base vectors V, V3, and V12, from the position and the orientation of the image position/orientation detection coil 44 obtained by a method to be described later.

The position/orientation calculation apparatus 4 as a position detection portion is connected to the image position/orientation detection coil 44 disposed in the rigid portion 21 of the ultrasound endoscope 2 via an A/D conversion apparatus 47 and is also electrically connected to a transmission antenna 41. The position/orientation calculation apparatus 4 is connected to a body surface detection coil 42 and a posture detection coil 43 respectively via A/D conversion apparatuses 45, 46. Moreover, the position/orientation calculation apparatus 4 is electrically connected to an image processing apparatus 5 via a cable of the RS-232C standard, for example.

The transmission antenna 41 includes a plurality of magnetic field generation coils of different winding axes orientation, not shown, and generates an alternating magnetic field in response to an output from the position/orientation calculation apparatus 4.

The A/D conversion apparatuses 45 to 47 include an amplifier, not shown, for amplifying an inputted signal, and an analog-digital conversion circuit, not shown, for sampling the amplified signal to convert the signal into digital data.

The image position/orientation detection coil 44 disposed in the rigid portion 21 of the ultrasound endoscope 2 detects the alternating magnetic field generated by the transmission antenna 41 and converts the detected alternating magnetic field into an position electric signal to output the position electric signal to the A/D conversion apparatus 47.

In addition, though details will be described later, the body surface detection coil 42 and the posture detection coil 43 include coils for detecting the alternating magnetic field generated by the transmission antenna 41 and convert the alternating magnetic field detected by the coils into a position electric signal to output the position electric signal to the A/D conversion apparatuses 45 and 46.

The position/orientation calculation apparatus 4 calculates the respective positions and the orientations of the image position/orientation detection coil 44, the body surface detection coil 42, and the posture detection coil 43 with respect to the transmission antenna 41, based on the position electric signals respectively outputted from the image position/orientation detection coil 44, the body surface detection coil 42, and the posture detection coil 43 and converted into digital data by the A/D conversion apparatuses 45 to 47.

As shown in FIG. 2, the posture detection coil 43 includes two coils having uniaxial winding axes disposed such that the winding axes are orthogonal to each other on the same plane. The orthonormal bases (unit vectors of the respective directions) W, W3, and W12 with an origin S fixed on the posture detection coil 43 are defined as shown in FIG. 2. That is, the base vectors parallel to the winding axes of the two coils disposed in the posture detection coil 43 are defined as W12 and W3. The posture detection coil 43 is mounted and fixed on the body surface of a subject 100 at a position close to an organ to be inspected by the ultrasound endoscope 2 by a tape, a belt, a band, an adhesive or negative pressure absorption, and the like, not shown.

The body surface detection coil 42 has a rod-like outer shape and includes inside one coil having uniaxial winding axis. The positional relationship between the distal end of the rod-like body surface detection coil 42 and the coil is fixed. Though details are described later, the body surface detection coil 42 is used such that an operator brings the distal end thereof into contact with feature points on a subject 100 (hereinafter the feature points on the body surface of the subject are simply referred to as body surface feature points).

Note that, the present embodiment is described assuming the body surface feature points as four feature points on the skeleton, that is, "xiphoid process", "left anterior superior iliac spine" on the left side of the pelvis, "right anterior superior iliac spine" on the right side of the pelvis, and "spinous process of vertebral body" in the middle of the left and right anterior superior iliac spines on the spine.

In the present embodiment, the positions of the four body surface feature points can be specified by the operator's palpation. Moreover, these four body surface feature points are not located on the same plane, so that the four points can form an oblique coordinate system with the xiphoid process set as the origin and with the three vectors directed to other feature points as fundamental vectors. Note that, the four body surface feature points are not limited to those shown in the present embodiment, and changed as needed depending on a medical instrument to be used and a region for which the medical instrument is used.

As shown in FIG. 3, the image processing apparatus 5 includes a matching circuit 61, an image index creation circuit 62, a communication circuit 51, reference image storage portion 52, an interpolation circuit 53, a three-dimensional human body image creation circuit 54, a synthesis circuit 63, a rotational transformation circuit 64, two three-dimensional guide image creation circuits (hereinafter referred to as a three-dimensional guide image creation circuit A65 and a three-dimensional guide image creation circuit B66), a mixing circuit 67, a display circuit 68, and a control circuit 60.

The control circuit 60 as a control portion includes an arithmetic device, a storage device, an input/output device and the like, and is electrically connected to each portion or each circuit in the image processing apparatus 5 via signal lines not shown to control the working of the image processing apparatus 5. Furthermore, in the present embodiment, the control circuit 60 controls also the workings of the ultrasound observation apparatus 3 and the position/orientation calculation apparatus 4.

The control circuit 60 is electrically connected with the input device 11 as an instruction portion. The input device 11 of the present embodiment includes a keyboard 12 and a mouse 13. The control circuit 60 controls the working of the medical guiding system 1 based on the instruction from the operator inputted through the input device 11. In the present embodiment, the keyboard 12 includes a switch group including display switching keys 12α, 12β, 12γ, an operation control key 12d, a body surface point obtaining key 12e, an in-vivo point obtaining key 12f, and a scanning region selection key 12g.

Note that the input device 11 is configured of the keyboard 12 and the mouse 13 in the present embodiment. However, this is one example of the input device and the input device is not limited to the one shown in the present embodiment. The input device 11 may be configured of a pointing device such as a trackball, a touch panel, or the like, or a switch such as a push switch, a rotary switch, or the like, for example. Furthermore, the input device 11 may be such one that the operator can input operation instruction by voice or gesture.

The reference image storage portion 52 is configured of a hard disk drive, a tape drive, and the like that are capable of storing a large volume of data, for example. In the reference image storage portion 52 are stored a plurality of reference image data RD as image information of a cross section of a human body. In addition, in the reference image storage portion 52 is stored a feature point list 101, shown in FIG. 5, on which names of the body surface feature points and the in-vivo feature points are listed.

The reference image data RD are obtained such that the data of human body tomographic image obtained from a predetermined human body by the X-ray three-dimensional helical CT apparatus 16, the three-dimensional MRI apparatus 15, or the like, and stored in a data center 17 is inputted to the image processing apparatus 5 via the network 14. The reference image data RD are data of tomographic images of square area with several tens of centimeters on a side of the cross section which is generally perpendicular to the body axis (linear axis passing through from the head to feet). The tomographic images are obtained at a pitch of 0.5 mm to several mm along the body axis.

Note that the reference image data RD may be obtained from the subject 100 himself/herself, or from a different human body. Moreover, the reference image data RD may be obtained from different human bodies in advance for each condition such as physical features of the human body including body height or body size, or sex, and the like. In addition, the reference image data RD may be directly inputted to the image processing apparatus 5 from the X-ray three-dimensional helical CT apparatus 16 or the three-dimensional MRI apparatus 15 via the network 14 to be stored in the reference image storage portion 52.

In the present embodiment, as shown in FIG. 4, in a group of a plurality of reference image data GRD obtained at a predetermined pitch along a body axis of a predetermined human body and stored in the reference image storage portion 52, the reference image data RD are attached with reference numerals 1 to N in the order from the foot direction. Here, in the reference image data shown in FIG. 4, the lower direction when facing the figure is the dorsal direction of the human body, and the depth direction from the front of the figure is the head direction of the human body.

Furthermore, the orthogonal coordinate axes O'-x'y'z' fixed with respect to the group of reference image data GRD and the orthonormal bases therefor (unit vectors of the respective axis directions) i', j', and k' are defined as shown in FIG. 4. Here, an origin O' is defined at lower leftmost of the reference image data RD attached with the reference numeral 1, and the x' axis and the y' axis are defined to be parallel to the lateral side and the longitudinal side, respectively. That is, the z' axis is parallel to the body axis.

The group of reference image data GRD of the present embodiment shown in FIG. 4 is configured of abdominal tomographic image data of the subject 100 himself/herself obtained by the X-ray three-dimensional helical CT apparatus 16. Under the effect of the X-ray contrast agent, the blood vessels such as an aorta 111, a superior mesenteric vein 112, and the like are displayed at a high luminance, the organs such as a pancreas 113 and the like which contain a large number of peripheral arteries are displayed at a medium luminance, and a duodenum 114 and the like are displayed at a low luminance.

Each of the interpolation circuit 53 and the synthesis circuit 63 includes a volume memory VM. For the convenience of description, hereinafter the volume memories provided to the interpolation circuit 53 and the synthesis circuit 63 are referred to as an interpolation memory 53a and a synthesis memory 63a, respectively. The interpolation memory 53a and the synthesis memory 63a as volume memories are capable of storing a large volume of data. To a partial storage region of the interpolation memory 53a and the synthesis memory 63a, a voxel space is assigned. As shown in FIG. 6, the voxel space is composed of memory cells (hereinafter referred to as voxels) having addresses corresponding to the orthogonal coordinate axes O'-x'y'z'.

The matching circuit 61 stores a correction condition table 102 defining correction conditions in a case of performing correction to be described later for each scanning region to be scanned by the ultrasound endoscope 2, as shown in FIG. 7.

The three-dimensional human body image creation circuit 54 and the rotational transformation circuit 64 incorporate a high-speed processor, not shown, that performs image processing such as extraction of voxels and pixels by luminance, rotational transformation, similarity transformation, and translation at high speed.

The display circuit 68 has a switch 69 for switching input thereto. The switch 69 has input terminals 69α, 69β, and 69γ, and one output terminal 69d. The input terminal 69α is electrically connected to the reference image storage portion 52. The input terminal 69β is electrically connected to an output terminal not shown of the optical observation apparatus 10. The input terminal 69γ is electrically connected to the mixing circuit 67. The output terminal 69d is electrically connected to the display apparatus 8.

Depressing one of the display switching keys 12α, 12β, and 12γ on the keyboard 12 by the operator causes the control circuit 60 to output an instruction to the display circuit 68 to switch the switch 69 to one of the input terminal 69α, 69β, and 69γ. Depressing the display switching key 12α allows the switch 69 to be switched to the input terminal 69α. Depressing the display switching key 12β allows the switch 69 to be switched to the input terminal 69β. Depressing the display switching key 12γ allows the switch 69 to be switched to the input terminal 69γ.

The display apparatus 8 includes an image display portion such as a cathode ray tube monitor, a liquid crystal monitor, or the like, to display an image based on a video signal on the image display portion.

Next, description will be made on the action of the medical guiding system 1 of the present embodiment having the above-described configuration.

Here, in FIGS. 1 and 3, the arrow lines respectively show flows of data of signals and data, which are attached with the following reference numerals a) to f) (hereinafter the signals and data are collectively referred to as information).

a) Flow of information related to an optical image indicated by dotted lines in the drawings
b) Flow of information related to an ultrasound tomographic image indicated by dashed lines in the drawings
c) Flow of information related to position and orientation indicated by solid lines in the drawings
d) Flow of information related to reference image data indicated by dashed-dotted lines in the drawings
e) Flow of information related to final display screen indicated by thick lines in the drawings
f) Flow of information related to controls other than the above indicated by the curved lines in the drawings Note that the above-described flows of information indicated by the respective arrow lines are only for describing a simple overview of the working, and the same kind of lines do not indicate the same data. That is, even if the kind of the arrow lines are the same in the drawings, the arrow lines located at positions different from each other indicate information having contents different from each other after subjected to conversion or processing in a previous circuit.

Below, first focusing on the six flows of information indicated in the above a) to f), the action of the medical guiding system 1 is described in line with the respective flows of information. After that, the whole action of the medical guiding system 1 is described in line with the actual operator's usage pattern.

First, the action of the present embodiment is described in line with the flows of information related to an optical image in the item a).

Illumination light is irradiated to a field of view of the image pickup apparatus 27 by an illumination apparatus, not shown, disposed in the rigid portion 21, and the image pickup apparatus 27 obtains an optical image within the field of view to output the obtained optical image as a CCD signal to the optical observation apparatus 10. The optical observation apparatus 10 creates image data based on the CCD signal to output the image data as optical image data to the input terminal 69β of the switch 69 of the display circuit 68 in the image processing apparatus 5.

Next, the action of the present embodiment is described in line with the flows of information related to the ultrasound tomographic image in the item b).

First, depressing the scan control key 12d by the operator causes the control circuit 60 to output a scan control signal to the ultrasound observation apparatus 3 to instruct start or stop of the radial scan. The ultrasound observation apparatus 3 selects some ultrasound transducers among a plurality of ultrasound transducers configuring the ultrasound transducer array 31, to transmit excitation signals having a shape like pulse voltages to the selected ultrasound transducers. The selected some ultrasound transducers receive the excitation signals to convert the signals into ultrasound of longitudinal waves as a medium. At this time, the ultrasound observation apparatus 3 delays the excitation signals so that the excitation signals reach the respective ultrasound transducers at different times. The excitation signals are delayed so that ultrasounds excited by the respective ultrasound transducers form one ultrasound beam when overlapped one another in the subject. The ultrasound beam is irradiated to the exterior of the ultrasound endoscope 2, and a reflected wave from the interior of the subject 100 returns to each of the ultrasound transducers via a path opposite to that of the ultrasound beam. Each of the ultrasound transducers converts the reflected wave into an electrical echo signal and outputs the echo signal to the ultrasound observation apparatus 3 via a path opposite to that of the excitation signal.

The ultrasound observation apparatus 3 reselects a plurality of ultrasound transducers to be involved in the formation of the ultrasound beam such that the ultrasound beam pivots in a plane (hereinafter radial scanning surface) which contains the center of the annulus of the ultrasound transducer array 31 and which is perpendicular to the insertion axis of the rigid portion 21, and then transmits excitation signals again to the selected ultrasound transducers. The transmission angle of the ultrasound beam thus changes. Repeating this achieves what is called a radial scan.

At this time, the ultrasound observation apparatus 3 creates a piece of digitalized ultrasound tomographic image data perpendicular to the insertion axis of the rigid portion 21 for one radial scan by the ultrasound transducer array 31, based on the echo signal converted from the reflected wave by the ultrasound transducers and then outputs the created ultrasound tomograpbic image data to the mixing circuit 67 in the image processing apparatus 5. At this time, the ultrasound observation apparatus 3 creates the ultrasound tomographic image data by processing the ultrasound tomogrpahic image data into a square.

Thus in the present embodiment, the ultrasound observation apparatus 3 reselects a plurality of ultrasound transducers to be involved in the formation of the ultrasound beam to transmit excitation signals again, so that the twelve o'clock direction of the square ultrasound tomographic image, for example, is determined depending on which of the ultrasound transducers is selected by the ultrasound observation apparatus 3 as the twelve o'clock direction to transmit excitation signals. Thus, the normal direction vector V, the three o'clock direction vector V3, and the twelve o'clock direction vector V12 of the ultrasound tomographic image are defined. In addition, the ultrasound observation apparatus 3 creates ultrasound tomographic image data through observation in −V direction opposite to that of the normal vector V.

The radial scan by the ultrasound transducer array 31 and the creation of the ultrasound tomographic image data and output of the ultrasound tomographic image data to the mixing circuit 67 by the ultrasound observation apparatus 3 are performed in real time during a period of time from when a scan start instruction is inputted by the depression of the scan control key 12d by the operator until scan termination instruction is inputted That is, in the present embodiment, the ultrasound tomographic image obtained by the ultrasound endoscope 2 is generated as a real time image.

Next, the action of the present embodiment is described in line with the flows of information related to the position and orientation in the item c).

The position/orientation calculation apparatus 4 excites a transmission coil not shown disposed in the transmission antenna 41 such that an alternating magnetic field is generated in the space. Two coils disposed in the image position/orientation detection coil 44, two coils disposed in the posture detection coil 43, and a coil disposed in the body surface detection coil 42 respectively detect the alternating magnetic field generated by the transmission antenna 41, and convert the alternating magnetic field into the position electric signals of the respective coils to output the position electric signals.

Next, the position/orientation calculation apparatus 4 calculates the position of the image position/orientation detection coil 44 and the directions of the base vectors V and V3, based on the position electric signal outputted from the image position/orientation detection coil 44 and converted into digital data by the A/D conversion apparatus 47. The position/orientation calculation apparatus 4 calculates the outer product of the orthogonal base vectors V and V3, thereby calculating the direction of the remaining base vector V12. Thus, the position and the orientation of the image position/orientation detection coil 44 with respect to the transmission antenna 41 are calculated.

Similarly, the position/orientation calculation apparatus 4 calculates the position of the posture detection coil 43 and the directions of the base vectors W12 and W3, based on the position electric signal outputted from the posture detection signal 43 and converted into digital data by the A/D conversion apparatus 46. The position/orientation calculation apparatus 4 calculates the outer product of the orthogonal base vectors W12 and W3, thereby calculating the direction of the remaining base vector W. Thus, the position and the orientation of the posture detection coil 43 with respect to the transmission antenna 41 are calculated.

In addition, the position/orientation calculation apparatus 4 calculates the position and the orientation of the body surface detection coil 42 with respect to the transmission antenna 41, based on the position electric signal outputted from the body surface detection coil 42 and converted into digital data by the A/D conversion apparatus 45.

Next, the position/orientation calculation apparatus 4 outputs the positions and the orientations of the image position/orientation detection coil 44, the posture detection coil 43, and the body surface detection coil 42 with respect to the transmission antenna 41 as position/orientation data to the matching circuit 61 in the image processing apparatus 5.

Here, details of the position/orientation data are described below. In the present embodiment, as shown in FIG. 8, the origin O is defined on the transmission antenna 41, and the orthogonal coordinate axes O-xyz and the orthonormal bases therefor (unit vectors of the respective directions) i, j, and k are defined in the real space in which the operator inspects the subject 100.

Then, it is assumed that the position of the image position/orientation detection coil 44 on the orthogonal coordinate axes O-xyz is O". Since the image position/orientation detection coil 44 is fixed in the vicinity of the center of the annulus ultrasound transducer array 31, the O" coincides with the center of the radial scan, that is, the center of the ultrasound tomographic image. Furthermore, the position of the posture detection coil 43 on the orthogonal coordinate axes O-xyz is assumed to be S and the position of the body surface detection coil 42 on the orthogonal coordinate axes O-xyz is assumed to be A.

That is, the position/orientation data contains positional information composed of the position O" of the image position/orientation detection coil 44, the position S of the posture detection coil 43, and the position A of the body surface detection coil 42, on the orthogonal coordinate axes O-xyz. In addition, the position/orientation data contains orientation information composed of the unit vectors V, V3, and V12 indicating the orientation of the image position/orientation detection coil 44, and the unit vectors W, W3, and W12 indicating the orientation of the posture detection coil 43, with respect to the orthogonal coordinate axes O-xyz.

Next, based on the above-described position/orientation data outputted from the position/orientation calculation apparatus 4 and the group of reference image data GRD, the matching circuit 61 calculates a first conversion equation and a second conversion equation for mapping the positions and the orientations expressed on the orthogonal coordinate axes O-xyz to the positions and the orientations in the voxel space expressed on the orthogonal coordinate axes O'-x'y'z'.

Specifically, based on the following first to fifth data groups, the matching circuit 61 calculates the first conversion equation and the second conversion equation for mapping the positions and the orientations expressed on the orthogonal coordinate axes O-xyz to the positions and the orientations in the voxel space expressed on the orthogonal coordinate axes O'-x'y'z'.

Here, the first data group includes the respective position vectors OA1, OA2, OA3, and OA 4 of the four body surface feature points A1, A2, A3, and A4 of the subject 100 on the orthogonal coordinate axes O-xyz. In the present embodiment, among the four body surface feature points, A1 is assumed to be the xiphoid process, A2 to be the left anterior superior iliac spine, A3 to be the right anterior superior iliac spine, and A4 to be the spinous process of vertebral body.

The positional information of these four body surface feature points A1, A2, A3, and A4 is calculated by the position/orientation calculation apparatus 4 when the operator specifies the positions of these points by palpation at the time of starting inspection and depressing the body surface point obtaining key 12e on the keyboard 12 while sequentially placing the body surface detection coil 42 on the body surface of the subject 100.

The second data group includes the position vector OS and unit vectors W, W3, and W12 expressing the orientation of the posture detection coil 43 on the orthogonal coordinate axes O-xyz.

The third data group includes the position vector OO" and the unit vectors V, V3, and V12 expressing the orientation of the image position/orientation detection coil 44 on the orthogonal coordinate axes O-xyz when the optical observation window 24 of the ultrasound endoscope 2 is brought into contact with each of the three feature points (hereinafter, only referred to as in-vivo feature points) P, Q, and R in the body of the subject 100. In the present embodiment, the in-vivo feature points are described on the feature point list 101 shown in FIG. 5, and the in-vivo feature points P, Q, and R represent the duodenal papilla, the cardia, and the pylorus, respectively.

The fourth data group includes position vectors O'A1', O'A2', O'A3', and O'A4' in the voxel space (orthogonal coordinate axes O'-x'y'z') of the four body surface feature points A1', A2', A3' and A4' in the group of reference image data GRD composed of a plurality of the 1st to N-th reference image data RD.

Here, the body surface feature points A1', A2', A3' and A4' in the group of reference image data GRD are regions anatomically equivalent to the body surface feature points A1, A2, A3, and A4 of the above-described subject 100. That is, in the present embodiment, the xiphoid process in the group of reference image data GRD is assumed to be the body surface feature point A1', the left anterior superior iliac spine to be A2', the right anterior superior iliac spine to be A3', and the spinous process of vertebral body to be A4'.

In the description below, the four body surface feature points in the group of reference image data GRD are attached with symbols with prime notations (also referred to as dash) and referred to as the reference image body surface feature points A1', A2', A3', and A4', respectively, in order to more clearly distinguish the points from the four body surface feature points A1 to A4 of the subject 100.

In the present embodiment, these four reference image body surface feature points A1', A2?', A3', and A4' are obtained by the operator specifying the relevant pixels on the group of reference image data GRD before starting the inspection.

The fifth data group includes position vectors O'P", O'Q", and O'R" in the voxel space (orthogonal coordinate axes O'-x'y'z') of three in-vivo feature points P", Q", and R" in the group of reference image data GRD composed of a plurality of the first to the N-th reference image data RD.

Here, the in-vivo feature points P", Q", and R" in the group of reference image data GRD are regions anatomically equivalent to the the above-described in-vivo feature points P, Q, and R of subject 100, respectively. That is, in the present embodiment, the duodenal papilla in the group of reference image data GRD is assumed to be in-vivo feature points P", the cardia to be Q", and the pylorus to be R".

In the description below, the three in-vivo feature points in the group of reference image data GRD are attached with symbols with double prime (also referred to as two dashes), and are referred to as the reference image in-vivo feature points P", Q", and R" in order to more clearly distinguish the feature points from the three in-vivo feature points P, Q, and R of the subject 100.

In the present embodiment, these three reference image in-vivo feature points P", Q", and R" are obtained by the operator specifying the relevant pixels on the group of reference image data GRD before starting the inspection.

Note that the reference image in-vivo feature points P", Q", and R" are obtained from the group of reference image data GRD similarly as the reference image body surface feature points A1', A2', A3' and A4'. However, it should be noted that the reference image in-vivo feature points are attached with the double prime, and the reference body surface feature points are attached with the prime.

Next, the matching circuit 61 maps the position/orientation data calculated on the orthogonal coordinate axes O-xyz based on the first and the second conversion equations, and calculates new position/orientation data on the orthogonal coordinate axes O'-x'y'z'.

Next, the matching circuit 61 outputs the new position/orientation data to the image index creation circuit 62 as position/orientation mapping data.

As shown in FIG. 9, the image index creation circuit 62 creates image index data 120 from the position/orientation mapping data with a total of six degrees of freedom including the position vector OO" of the position O" of the image position/orientation detection coil 44, on the orthogonal coordinate axes O-xyz, and the unit vectors V, V3, and V12 indicating the orientation of the image position/orientation detection coil 44 with respect to the orthogonal coordinate axes O-xyz. The image index creation circuit 62 then outputs the image index data 120 to the synthesis circuit 63.

The image index data 120 is image data on the orthogonal coordinate axes O'-x'y'z' in which a parallelogrammatic ultrasound tomographic image marker 121 is synthesized with a blue distal direction marker 122 and a yellowish green arrow-shaped six o'clock direction marker 123. The image index data 120 is an indicator expressing the position and orientation of the radial scanning surface on the orthogonal coordinate axes O'-x'y'z', and the ultrasound tomographic image marker 121, the distal direction marker 122, and the six o'clock direction marker 123 show the radial scanning surface, the insertion direction of the rigid portion 21, and the six o'clock direction of the radial scan, respectively.

Next, the action of the present embodiment is described in line with the flows of information related to the reference image data in the item d).

First, when the operator depresses a predetermined key on the keyboard 12, or selects a menu displayed on the display apparatus 8 by the mouse 13, instruction to obtain the group of reference image data GRD is inputted to the control circuit 60. At this time, the operator instructs an acquisition source of the group of reference image data GRD at the same time. In response to the instruction, the control circuit 60 issues an instruction on loading of the group of reference image data GRD and the acquisition source thereof to the communication circuit 51.

In a case where the acquisition source is the X-ray three-dimensional helical CT apparatus 16, for example, the communication circuit 51 loads a plurality of two-dimensional CT images (reference image data RD) as the group of reference image data GRD through the network 14 to cause the reference image storage portion 52 to store the data. Also in a case where the acquisition source is the three-dimensional MRI apparatus 15 or the data center 17, the communication circuit 51 similarly loads a plurality of reference image data RD through the network 14 to cause the reference image storage portion 52 to store the data as the group of reference image data GRD.

Since the actions are the same in either case where the operator selects the X-ray three-dimensional helical CT apparatus 16, or the operator selects the three-dimensional MRI apparatus 15 or the data center 17 as data acquisition source in the present embodiment, the action will be described only on the case where the operator selects the X-ray three-dimensional helical CT apparatus 16 as the acquisition source.

As shown in FIG. 4, on the group of reference image data RD, under the effect of the X-ray contrast agent, the blood vessels such as the aorta 111 and the superior mesenteric vein 112 are displayed at a high luminance, the organ such as the pancreas 113 which contains a large number of peripheral arteries is displayed at a medium luminance, and the duodenum 114 and the like are displayed at a low luminance.

The interpolation circuit 53 reads out the group of reference image data GRD including all the first to N-th reference image data RD from the reference image storage portion 52, to fill the reference image data in the voxel space in the interpolation memory 53a. Specifically, the interpolation circuit 53 outputs the luminance of each of the pixels in the reference image data RD to the voxels having addresses corresponding to the pixels.

Next, the interpolation circuit 53 calculates and interpolates the luminance of the voxels located between the adjacent reference image data RD, based on the luminance of the adjacent reference image data RD, to fill empty voxels with the data. Thus, all the voxels in the voxel space is filled with the data based on the group of reference image data GRD (hereinafter referred to as voxel data).

The three-dimensional human body image creation circuit 54 extracts voxels with a high lumince value (mostly blood vessels) and voxels with a medium luminance value (mostly the organ such as the pancreas which contains a large number of peripheral blood vessels) according to the luminance value range from the interpolation circuit 53, and classifies the voxels into each luminance to color the voxels. Next, the three-dimensional human body image creation circuit 54 fills the extracted voxels as the three-dimensional human body image data in the voxel space of the synthesis memory 63a in the synthesis circuit 63. At this time, the three-dimensional human body image creation circuit 54 fills the voxel space with the extracted voxels so that the address of each extracted voxel in the voxel space in the interpolation memory 53a becomes the same as that in the voxel space in the synthesis memory 63a.

The three-dimensional human body image data is shown in FIG. 10. In the three-dimensional human body image data are extracted the aorta 111 and the superior mesenteric vein 112 as blood vessels displayed at a high luminance, and the pancreas 113 as the organ displayed at a medium luminance, and the aorta 111 and the superior mesenteric vein 112 are colored in red, and the pancreas 113 is colored in green. In addition, the three-dimensional human body image data is three-dimensional data of when the subject 100 is observed from the ventral side with the head side on the right, and the foot side on the left.

Then, the synthesis circuit 63 fills the image index data 120 in the voxel space in the synthesis memory 63a. Thus the synthesis circuit 63 fills the three-dimensional human body image data and the image index data 120 into the same voxel space in the synthesis memory 63a, to synthesize these data into one set of data. Hereinafter, the synthetic data of the three-dimensional human body image data and the image index data 120 created by the synthesis circuit 63 is referred to as synthetic three-dimensional data.

The rotational transformation circuit 64 reads out the synthetic three-dimensional data to execute a rotation processing on the synthetic three-dimensional data based on the position/orientation mapping data such that a normal line of the ultrasound tomographic image marker 121 coincides with an observation line of sight of the operator, that is, a normal line of the screen of the display apparatus 8 and the six o'clock direction marker orients in downward direction of the screen of the display apparatus.

The three-dimensional guide image creation circuit A65 executes a rendering processing such as hidden surface removal or shading on the synthetic three-dimensional data to create image data (hereinafter referred to as three-dimensional guide image data 81) that can be outputted to the display apparatus 8. Here, the initial orientation of the three-dimensional guide image data 81 at the time of creation thereof is such that a viewpoint is set for observation from the ventral side. That is, the three-dimensional guide image creation circuit A65 creates the three-dimensional guide image data 81 of when the subject 100 is observed from the ventral side as shown in FIG. 11, to output the created three-dimensional guide image data 81 to the mixing circuit 67. In FIG. 11, the right side facing the drawing is a head side of the subject 100, and the left side is the foot side.

The three-dimensional guide image creation circuit B66 executes a rendering processing such as hidden surface removal or shading on the synthetic three-dimensional data subjected to the rotational processing to create the three-dimensional guide image data 82 that can be outputted to the display apparatus 8. In the present embodiment, as an example, the three-dimensional guide image creation circuit B66 creates the three-dimensional guide image data 82 in which the normal line of the ultrasound tomographic image marker 121 coincides with the observation line of sight of the operator, that is, the normal line of the screen of the display apparatus 8 and the six o'clock direction marker 123 is set so as to orient downward on the screen of the display apparatus 8, as shown in FIG. 12. The three-dimensional guide image creation circuit B66 outputs to the mixing circuit 67 the three-dimensional guide image data 82 in which the normal line of the ultrasound tomographic image marker 121 coincides with that on the screen.

Note that, in the three-dimensional guide image data 82 shown in FIG. 13, the three-dimensional human body image data located on nearer side than the ultrasound tomographic image marker 121 is not displayed, and a cross section of the three-dimensional human body image data located on the ultrasound tomographic image marker 121 is displayed. In addition, the ultrasound tomographic image marker 121 among the image index data 120 is displayed to be translucent so that the three-dimensional human body image data behind the ultrasound tomographic image marker 121 can be seen through.

Next, the action of the present embodiment is described in line with the flows of information related to the final screen display in the item e).

The mixing circuit 67 creates mixing data for adjacently displaying the ultrasound tomographic image data 83 from the ultrasound observation apparatus 3, three-dimensional guide image data 61 of when the subject is observed from the ventral side, from the three-dimensional guide image creation circuit A65, and the three-dimensional guide image data 82 in which the normal line of the ultrasound tomographic image marker 121 coincides with that on the screen, from the three-dimensional guide image creation circuit B66.

The display circuit 68 converts the mixing data into analog video signal.

Based on the analog video signal outputted from the display circuit 68, the display apparatus 8 adjacently displays the ultrasound tomographic image 83, the three-dimensional guide image 82 of when the subject is observed from the foot side, and the three-dimensional guide image 81 of when the subject is observed from the ventral side, as shown in FIG. 13. The organs respectively expressed on the three-dimensional guide images 81 and 82 are displayed in different colors on the display apparatus 8.

Next, the action of the present embodiment is described in line with the flows of information related to control in the item f).

The matching circuit 61, the image index creation circuit 62, the communication circuit 51, the reference image storage portion 52, the interpolation circuit 53, the three-dimensional human body image creation circuit 54, the synthesis circuit 63, the rotational transformation circuit 64, the three-dimensional guide image creation circuit A65, the three-dimensional guide image creation circuit B66, the mixing circuit 67, and the display circuit 68 in the image processing apparatus 5 are controlled by the instruction from the control circuit 60 according to a flowchart to be described in detail later.

Figure 14:
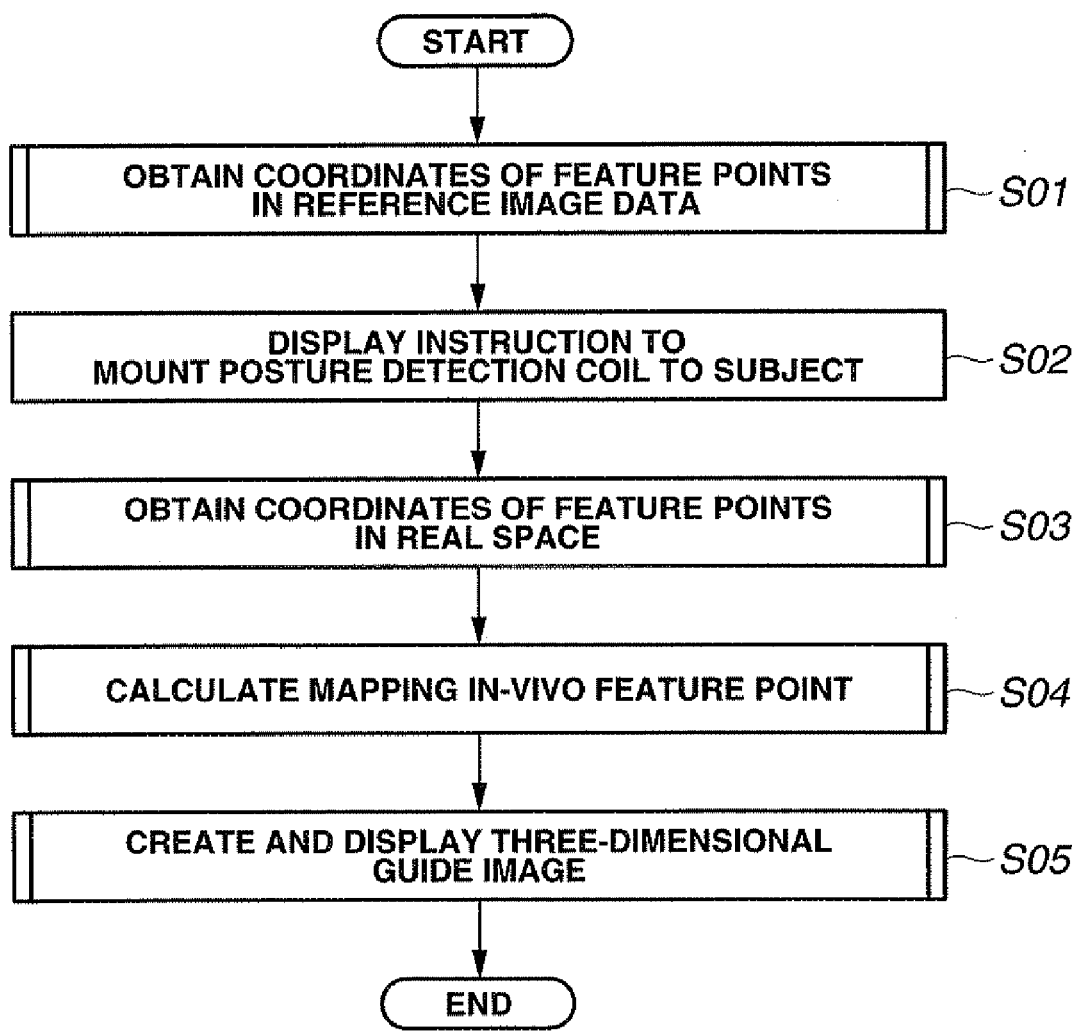
FIG. 14 is a flowchart of a main routine showing the whole working of the medical guiding system.

The action of the medical guiding system 1 according to the present embodiment is described below. Note that the following description on the action will be made in line with the actual usage pattern by the operator. FIG. 14 is a flowchart of the main routine indicating the whole working of the medical guiding system.

First, the control circuit 60 sets a plurality of reference image body surface feature points and the reference image in-vivo feature points in the group of reference image data GRD by the instruction input by the operator or automatic calculation, to execute processing to obtain the coordinates of the reference image body surface feature points and the reference image in-vivo feature points in the voxel space, in other words, on the orthogonal coordinate axes O-x'y'z' (step S01). The above-described fourth and fifth data groups are obtained in the step S01, which will be detailed later with reference to the flowchart in FIG. 15.

In the present embodiment, as described above, the reference image body surface feature points on the group of reference image data GRD are four points, that is, the xiphoid process (A1'), the left anterior superior iliac spine (A2'), the right anterior superior iliac spine (A3'), and the spinous process of vertebral body (A4'), and the reference image in-vivo feature points are three points, that is, the duodenal papilla (P"), the cardia (Q"), and the pylorus (R").

Next, the control circuit 60 causes the display apparatus 8 to perform a display to prompt the operator to mount the posture detection coil 43 to the subject 100 (step S02). The operator mounts the posture detection coil 43 on the body surface of the subject 100 at a position in the vicinity of the region to be inspected to fix the coil. That is, in the step S02, the above-described second data group can be obtained.

Next, the control circuit 60 executes a processing of obtaining the position/orientation data of the body surface feature points and the in-vivo feature points in the real space, that is, on the orthogonal coordinate axes O-xyz (step S03). The first, second, and third data groups are obtained in the step S03, which will be detailed later with reference to the flowchart in FIG. 16.

Next, the control circuit 60 calculates the first conversion equation for mapping the position/orientation data of an arbitrary point expressed on the orthogonal coordinate axes O-xyz into the position/orientation mapping data in the voxel space expressed on the orthogonal coordinate axes O'-x'y'z'. Then, based on the first conversion equation, the control circuit 60 obtains in-vivo feature point position mapping data in which the position data of the in-vivo feature points expressed on the orthogonal coordinate axes O-xyz is mapped into the voxel space expressed on the orthogonal coordinate axes O'-x'y'z' (step S04). The processing procedures in the step S04 will be described later in detail with reference to the flowchart in FIG. 17.

Next, the control circuit 60 executes a three-dimensional guide image creation display processing in which the three-dimensional guide images 81, 82 are created to assist the operation of the ultrasound endoscope 2 by the operator and the ultrasound tomographic image 83, the three-dimensional guide images 81, 82 are adjacently displayed on the screen of the display apparatus 8, as shown in FIG. 13 (step S05). The processing procedures in the step S05 will be described later in detail with reference to the flowchart in FIG. 18.

Next, description will be made below, with reference to the flowchart in FIG. 15, on the detail of the obtaining processing of the plurality of reference image body surface feature points and the reference image in-vivo feature points in the group of reference image data GRD in the step S01 in the flowchart shown in FIG. 14.

First, depressing the display switching key 12α on the keyboard 12 by the operator causes the control circuit 60 to switch the switch 69 of the display circuit 68 to the input terminal 69α (step S11). This allows a part or the entirety of the group of reference image data GRD stored in the reference image storage portion 52 to be displayed on the screen of the display apparatus 8.

Next, the control circuit 60 causes the display circuit 68 to read out any one of the 1st to the N-th reference image data RD selected through the input instruction by the operator from the group of reference image data GRD stored in the reference image storage portion 52 and to output an analog video signal such that the reference image data RD is displayed on the display apparatus 8 (step S12). This allows the reference image data RD selected by the operator to be displayed on the screen of the display apparatus 8.

Next, the control circuit 60 performs a display to prompt the operator to select a pixel corresponding to any one of the four body surface feature points in the feature point list 101 shown in FIG. 5 on the reference image data RD displayed on the display apparatus 8. The control circuit 60 then obtains and stores the coordinates of the predetermined pixel selected by the operator on the predetermined reference image data RD, and the name of the body surface feature point corresponding to the predetermined pixel (step S13).

Note that, the name of the body surface feature point obtained here do not necessarily have to be a specific name like the "xiphoid process", and it is needless to say that the name may be an ID composed of unique numeric characters, letters, and the like bound with the name of the body surface feature point.

Next, the control circuit 60 judges whether or not the coordinates on the reference image data RD of the pixels corresponding to all the four body surface feature points in the feature point list 101 have been obtained (step S14). When the coordinates of the pixels corresponding to all the body surface feature points in the feature point list 101 have been obtained here, the procedure moves on to step S15, and when the coordinates of the pixels corresponding to all the body surface feature points have not been obtained, the procedure goes back to the step S12.

When determining that the coordinates of the pixels corresponding to all the body surface feature points have been obtained in the step S14, the control circuit 60 next causes the display circuit 68 to read out any one of the 1st to the N-th reference image data selected through the input instruction by the operator from the group of reference image data GRD stored in the reference image storage portion 52, and to output an analog video signal to display the reference image data RD on the display apparatus 8 (step S15). This allows the reference image data RD selected by the operator to be displayed on the screen of the display apparatus 8.

Next, the control circuit 60 performs a display to prompt the operator to select a pixel corresponding to any one of the three in-vivo feature points in the feature point list 101 shown in FIG. 5 on the reference image data RD displayed on the display apparatus 8 The control circuit 60 then obtains and stores the coordinates of the predetermined pixel selected by the operator on the predetermined reference image data RD, and the name of the in-vivo feature point corresponding to the predetermined pixel (step S16).

Next, the control circuit 60 judges whether or not the coordinates on the reference image data RD of the pixels corresponding to all the three in-vivo feature points in the feature point list 101 have been obtained (step S17). When the coordinates of the pixels corresponding to all the in-vivo feature points in the feature point list 101 have been obtained here, the procedure moves on to step S18, and when the coordinates of the pixels corresponding to all the in-vivo feature points have not been obtained, the procedure goes back to the step S15.

When determining that the coordinates of the pixels corresponding to all the in-vivo feature points have been obtained in step S17, the control circuit 60 next calculates the coordinates in the voxel space, that is, the coordinates on the orthogonal coordinate axes O'-x'y'z' of the pixels corresponding to the respective body surface feature points obtained in the step S13 and the coordinates of the pixels corresponding to the respective in-vivo feature points obtained in the step S16, to cause the matching circuit 61 to store the calculated coordinates (step S18).

With the above-described procedures, the coordinates of the reference image body surface feature points A1', A2', A3', and A4' in the voxel space (on the orthogonal coordinate axes O'-x'y'z') as the fourth data group and the coordinates of the reference image in-vivo feature points P''', Q''', and R''' in the voxel space (on the orthogonal coordinate axes O'-x'y'z') as the fifth data group are obtained and stored in the matching circuit. Then the procedure returns to the main routine shown by the flowchart in FIG. 14.

Figure 15:
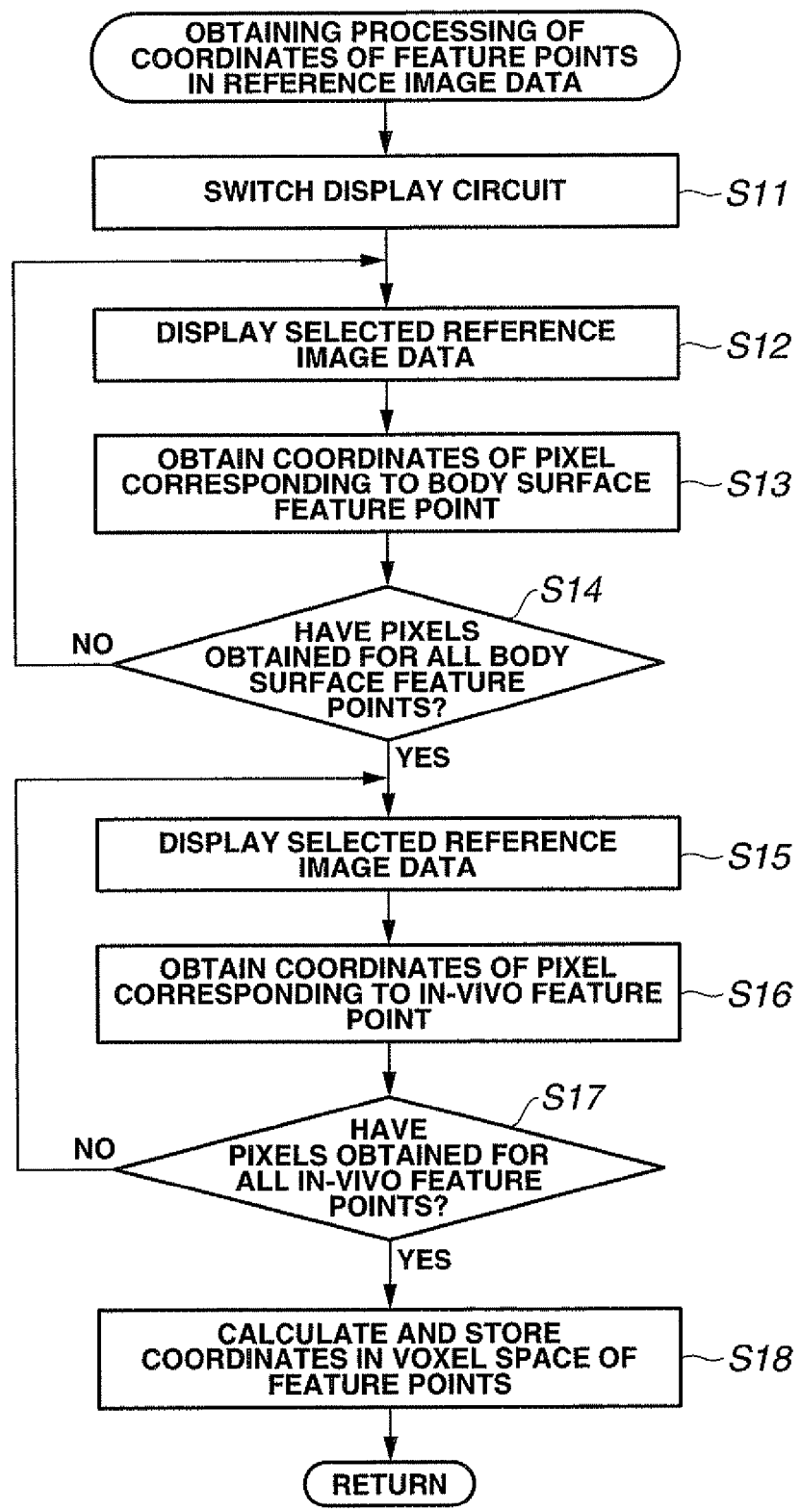
FIG. 15 is a flowchart of a coordinate obtaining processing of feature points on the reference image data.

The specific usage pattern by the operator of the medical guiding system 1 according to the present embodiment in the processing shown by the flowchart in FIG. 15 is as follows.

First, in the step S11, the operator depresses the display switching key 12α on the keyboard 12. This operation allows the switch 69 of the display circuit 68 to be switched.

Next, in the step S12, the operator selects one reference image data RD from the group of reference image data GRD using the keyboard 12 or the mouse 13. This operation allows the reference image data RD selected by the operator to be displayed on the screen of the display apparatus 8. Here, when the reference image data RD displayed on the display apparatus 8 does not contain any one of the four body surface feature points, that is, the xiphoid process, the left anterior superior iliac spine, the right anterior superior iliac spine, and the spinous process of vertebral body, the operator reselects another reference image data RD, and repeats selection of different reference image data RD until the reference image data containing any one of the four body surface feature points is displayed.

Next, in the step S13, the operator specifies the pixel corresponding to a body surface point closest to any one of the four body surface feature points on the reference image data RD displayed on the display apparatus 8, by using the keyboard 12 or the mouse 13. When the operator performs specifying operation of the pixel corresponding to the body surface feature point, the control circuit 60 causes the feature point list 101 shown in FIG. 5 to be displayed on the screen of the display apparatus 8.

Then, the operator selects the name of the body surface feature point corresponding to the pixel specified before, from the feature point list 101 displayed on the display apparatus 8, using the keyboard 12 or the mouse 13. This operation causes the control circuit 60 to recognize and obtain the correspondence of the specified pixel corresponding to the body surface feature point to which coordinates on what number of the N pieces of reference image data RD configuring the group of reference image data GRD.

Then the above-described steps S12 and S13 are repeated for all the four body surface feature points. Thus completes the specifying step of the pixels on the reference image data RD corresponding to all the four reference image body surface feature points A1', A2', A3', and A4' by the operator (YES in the step S14).

Figure 19:
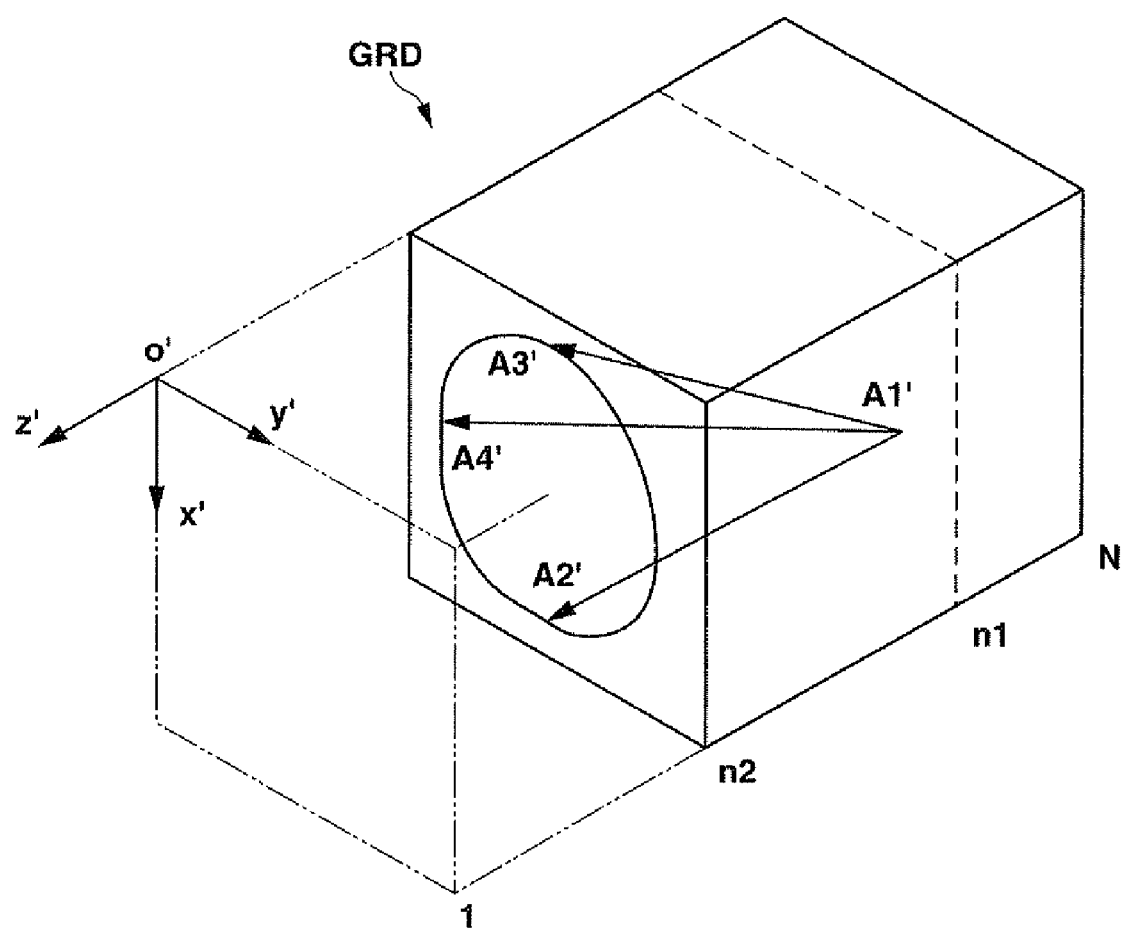
FIG. 19 is a pattern diagram showing a concept of reference image body surface feature points in a group of reference image data.

FIG. 19 shows a pattern diagram indicating a concept of the reference image body surface feature points in the group of reference image data GRD. In the present embodiment, for the convenience of description, description is made assuming that the xiphoid process (A1') is contained in the n1-th reference image data RD, and the left anterior superior iliac spine (A2'), the right anterior superior iliac spine (A3'), and the spinous process of vertebral body (A4') are contained in the n2-th reference image data RD, as shown in FIG. 19. Here, n1 and n2 are natural numbers which are not larger than N.

Next, in the step S15, the operator selects one reference image data RD from the group of reference image data GRD using the keyboard 12 or the mouse 13. This operation allows the reference image data RD selected by the operator to be displayed on the screen of the display apparatus 8. Here, when the reference image data RD displayed on the display apparatus 8 does not contain any one of the three in-vivo feature points, that is, the duodenal papilla, the cardia, and the pylorus, the operator reselects another reference image data RD, and repeats selection of different reference image data RD until the reference image data containing any one of the three in-vivo feature points is displayed.

Next, in the step S16, the operator specifies the pixel closest to any one of the three in-vivo feature points on the reference image data RD displayed on the display apparatus 8, using the keyboard 12 or the mouse 13. When the operator performs specifying operation of the pixel corresponding to the in-vivo feature point, the control circuit 60 causes the feature point list 101 shown in FIG. 5 to be displayed on the screen of the display apparatus 8.

Then, the operator selects the name of the in-vivo feature point corresponding to the pixel specified before, from the feature point list 101 displayed on the display apparatus 8, using the keyboard 12 or the mouse 13. This operation causes the control circuit 60 to obtain the correspondence of the specified pixel corresponding to the in-vivo feature point to which coordinates on what number of the N pieces of reference image data RD configuring the group of reference image data GRD.

Then, the above-described steps S15 and S16 are repeated for all the three in-vivo feature points. Thus completes the specifying step of the pixels on the reference image data RD corresponding to all the three reference image in-vivo feature points P", Q", and R" by the operator (YES in the step S17).

Next, in step S18, the control circuit 60 calculates the coordinates on the orthogonal coordinate axes O'-x'y'z' of the respective pixels corresponding to the four reference image body surface feature points A1', A2', A3', and A4', and the respective pixels corresponding to the three reference image in-vivo feature points P", Q", and R".

Thus, the above-described fourth and fifth data groups are obtained by the medical guiding system 1.

Next, description is made below, with reference to the flowchart in FIG. 16, on the detail of the obtaining processing of the positional information of a plurality of body surface feature points and in-vivo feature points in the real space in the step S03 in the flowchart shown in FIG. 14.

First, the control circuit 60 performs a display on the display apparatus 8 to prompt the operator to bring the body surface detection coil 42 into contact with any one of the four body surface feature points of the subject 100 (step S31). In the present embodiment, as described above, the four body surface feature points are xiphoid process (A1), the left anterior superior iliac spine (A2), the right anterior superior iliac spine (A3), and the spinous process of vertebral body (A4).

Next, the control circuit 60 instructs the matching circuit 61 to calculate the positions and the orientations of the body surface detection coil 42 and the posture detection coil 43 with respect to the transmission antenna 41 at the timing that the body surface point obtaining key 12e was depressed by the operator (step S32).

Next, the control circuit 60 displays the feature point list 101 shown in FIG. 5 on the display apparatus 8, and performs a display to prompt the operator to select from the feature point list 101 the region with which the body surface detection coil 42 was brought into contact in the immediately preceding step S32. Then, the control circuit 60 obtains the name of the body surface feature point selected by the operator and stores the obtained name (step S33). Note that the name of the body surface feature point obtained here do not necessarily have to be a specific name like the "xiphoid process", and it is needless to say that the name may be an ID composed of unique numeric characters, letters, and the like bound with the name of the body surface feature point.

Next, the control circuit 60 associates the positions and the orientations of the body surface detection coil 42 and the posture detection coil 43 with respect to the transmission antenna 41 obtained in the step S32 with the name of the body surface feature point obtained in the step S33, to cause the matching circuit 61 to store the position/orientation data and the name of the body surface feature point (step S34).

Then, the control circuit 60 judges whether or not information on positions and orientations of the body surface detection coil 42 and the posture detection coil 43 with respect to the transmission antenna 41 has been obtained for all of the body surface feature points in the feature point list 101 (step S35). When the information on the positions and the orientations of the body surface detection coil 42 and the posture detection coil 43 with respect to the transmission antenna 41 has been obtained for all of the body surface feature points in the feature point list 101 here, the procedure moves on to step S36, otherwise the procedure goes back to the step S31.

When determining that the information on the positions and the orientations of the body surface detection coil 42 and the posture detection coil 43 with respect to the transmission antenna 41 has been obtained for all of the body surface feature points in the step S35, the control circuit 60 then switches the switch 69 of the display circuit 68 to the input terminal 69b. This allows an optical observation image obtained by the image pickup apparatus 27 to be displayed on the display circuit 8. In addition, the control circuit 60 performs a display to prompt the operator to insert the rigid portion 21 and the flexible portion 22 of the ultrasound endoscope 2 into the body of the subject 100 (step S36).

Next, the control circuit 60 performs a display on the display apparatus 8 to prompt the operator to bring the optical observation window 24 of the rigid portion 21 into contact with any one of the three in-vivo feature points of the subject 100 (step S37). In the present embodiment, as described above, the three in-vivo feature points are the duodenal papilla (P), the cardia (Q), and the pylorus (R).

Next, the control circuit 60 instructs the matching circuit 61 to calculate the positions and the orientations of the image position/orientation detection coil 44 and the posture detection coil 43 with respect to the transmission antenna 41 at the timing that the in-vivo point obtaining key 12f was depressed by the operator (step S38).

The control circuit 60 then displays the feature point list 101 shown in FIG. 5 on the display apparatus 8, and performs a display to prompt the operator to select from the feature point list 101 the region with which the optical observation window 24 was brought into contact in the immediately preceding step S38. The control circuit 60 then obtains the name of the in-vivo feature point selected by the operator and stores the name (step S39).

Next, the control circuit 60 associates the positions and the orientations of the image position/orientation detection coil 44 and the posture detection coil 43 with respect to the transmission antenna 41 obtained in the step S38 with the name of the in-vivo feature point obtained in the step S39, to cause the matching circuit 61 to store the position/orientation data and the name of the body surface feature point (step S40).

Next, the control circuit 60 judges whether or not information on the positions and the orientations of the image position/orientation detection coil 44 and the posture detection coil 43 with respect to the transmission antenna 41 has been obtained for all of the three in-vivo feature points in the feature point list 101 (step S41). When the information on the positions and the orientations of the image position/orientation detection coil 44 and the posture detection coil 43 with respect to the transmission antenna 41 has been obtained for all of the in-vivo feature points in the feature point list 101 here, the procedure returns to the main routine shown by the flowchart in FIG. 14, otherwise the procedure goes back to the step S37.

Figure 16:
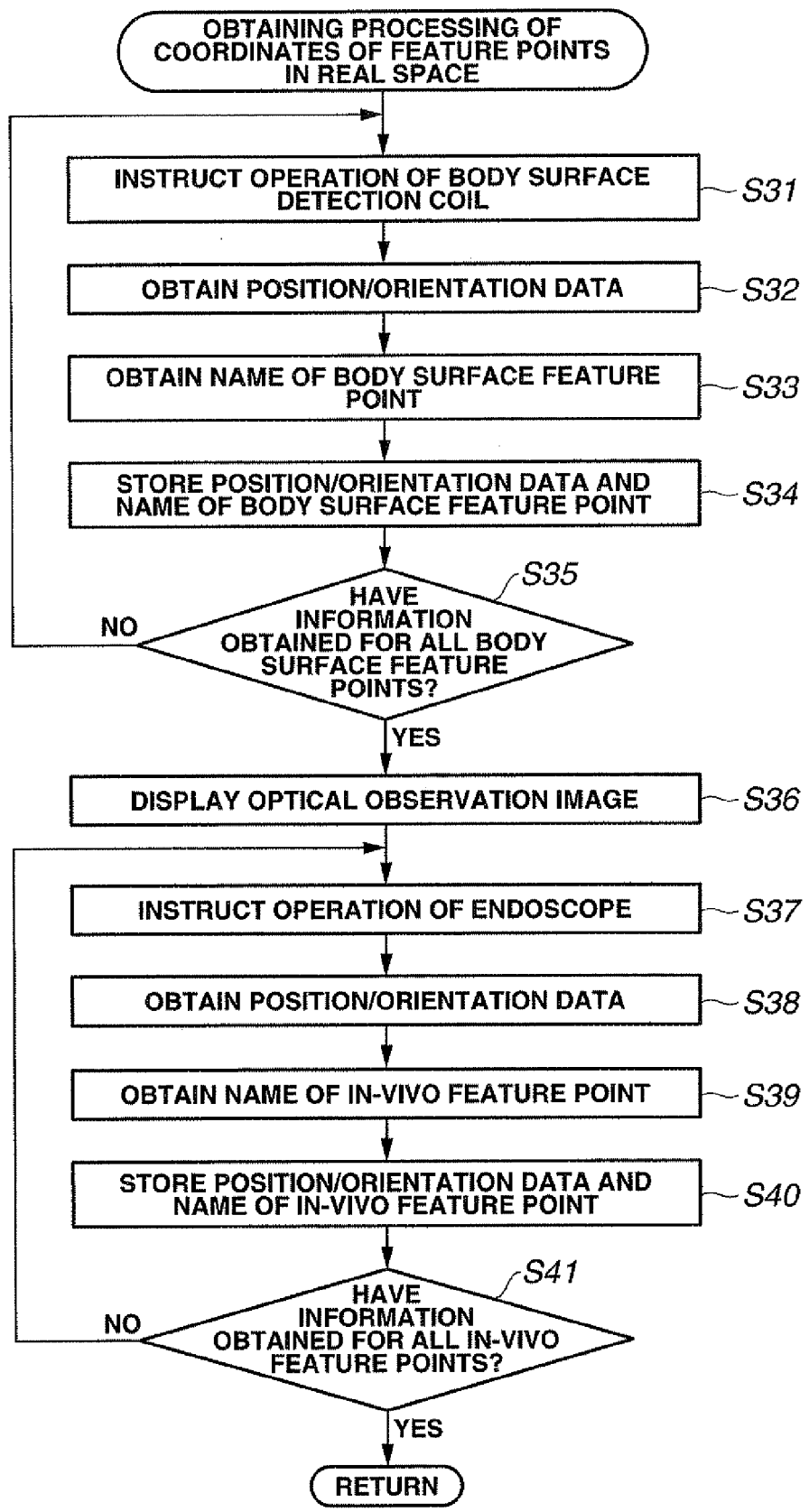
FIG. 16 is a flowchart of a coordinate obtaining processing of feature points in a real space.

In the processing shown by the flowchart in FIG. 16, the first data group is obtained first by the medical guiding system 1 in the steps S31 to S35, and the third data group is obtained in the steps S36 to S41.

The specific usage pattern by the operator of the medical guiding system 1 according to the present embodiment in the processing shown by the flowchart in FIG. 16 is as follows.

First, in the step S31, the operator palpates the subject 100 to bring the body surface detection coil 42 into contact with a body surface position closest to one of the four body surface feature points, that is, the xiphoid process, the left anterior superior iliac spine, the right anterior superior iliac spine, and the spinous process of vertebral body.

Next, in the step S32, the operator depresses the body surface point obtaining key 12e leaving the body surface detection coil 42 in contact with the body surface feature point of the subject 100. The operation causes the matching circuit 61 to calculate the positions and orientations of the body surface detection coil 42 and the posture detection coil 43, and causes the control circuit 60 to obtain the positions and orientations.

Next, in the step S33, the operator selects, from the feature point list 101 displayed on the display apparatus 8, the name of the body surface feature point with which the body surface detection coil 42 was brought into contact before, using the keyboard 12 or the mouse 13. This operation causes the control circuit 60 to obtain the name of the body surface feature point selected by the operator.

Next, in the step S34, the name of the body surface feature point selected by the operator in step S33 and the information on the positions and orientations of the body surface detection coil 42 and the posture detection coil 43 obtained in the step S32 are associated with each other, to be stored in the matching circuit 61.

Then, the above-described steps S31 to S34 are repeated for all the four body surface feature points A1, A2, A3, and A4. Thus completes the obtaining processing of the positions of the body surface feature points A1, A2, A3, and A4 in the real space (the orthogonal coordinate axes O-xyz).

Next, in the step S36, the operator inserts the rigid portion 21 and the flexible portion 22 of the ultrasound endoscope 2 into the body of the subject 100, while referring to the optical observation image displayed on the display apparatus 8.

Next, in the step S37, the operator brings the optical observation window 24 into contact with the vicinity of one of the three in-vivo feature points, that is, the duodenal papilla, the cardia, and the pylorus, while referring to the optical observation image of inside of the body of the subject 100 displayed on the display apparatus 8.

Next, in the step S38, the operator depresses the in-vivo point obtaining key 12f while keeping the optical observation window 24 in contact with the in-vivo feature point of the subject 100. The operation causes the matching circuit 61 to calculate the positions and orientations of the image position/orientation detection coil 44 and the posture detection coil 43, and causes the control circuit 60 to obtain the positions and orientations.

Next, in the step S39, the operator selects, from the feature point list 101 displayed on the display apparatus 8, the name of the in-vivo feature point with which the optical observation window 24 was brought into contact before, using the keyboard 12 or the mouse 13. This operation causes the control circuit 60 to obtain the name of the in-vivo feature point selected by the operator.

Next, in the step S40, the name of the in-vivo feature point selected by the operator in the step S39 and the information on positions and orientations of the image position/orientation detection coil 44 and the posture detection coil 43 obtained in the step 838 are associated with each other, to be stored in the matching circuit 61.

Then, the above-described steps S36 to S40 are repeated for all the three in-vivo feature points P, Q, and R. Thus completes the obtaining processing of the positions of the in-vivo feature points P, Q, and R in the real space (the orthogonal coordinate axes O-xyz).

With the above-described procedures, the first, the second, and the third data groups are obtained by the medical guiding system 1.

Next, description is made below, with reference to the flowchart in FIG. 17, on the details of calculation processing of the mapping in-vivo feature point in the step S04 of the flowchart shown in FIG. 14.

First, the control circuit 60 instructs the matching circuit 61 to calculate the first conversion equation for obtaining the first mapping in which the position and the orientation in the real space expressed on the orthogonal coordinate axes O-xyz are described on the orthogonal coordinate axes O'-x'y'z', that is, in the voxel space (step S51).

Here, the first mapping and the first conversion equation are specifically defined as follows. FIG. 20 is a view for describing the first mapping.

As shown in FIG. 20, by using the body surface feature points A1, A2, A3, and A4, an oblique coordinate system A1-A2 A3 A4 with the three vectors directed from the xiphoid process (A1) to the other body surface feature points (A2, A3, and A4) as fundamental vectors is first defined in the real space (orthogonal coordinate axes O-xyz). Similarly, by using the reference image body surface feature points A1', A2', A3', and A4', an oblique coordinate system A1'-A2'A3'A4' with the three vectors directed from the xiphoid process (A1') to the other body surface feature points (A2', A3', and A4') as fundamental vectors is defined in the voxel space (orthogonal coordinate axes O'-x'y'z').

The oblique coordinate system A1-A2 A3 A4 is defined in the real space, that is, on the subject 100, and the oblique coordinate system A1'-A2'A3'A4' is defined in the voxel space. Note that the voxel space means, as described above, a data space obtained by interpolating the group of reference image data GRD.

Furthermore, the first mapping means a mapping from the real space to the voxel space such that "the coordinates of an arbitrary point on the orthogonal coordinate axes O-xyz, which are expressed by the oblique coordinate system A1-A2 A3 A4 on the subject 100 (real space)" are the same as "the coordinates on the orthogonal coordinate axes O'-x'y'z' of a point resulting from the mapping of the arbitrary point, which are expressed by the oblique coordinate system A1'-A2'A3'A4' in the voxel space". Moreover, the first conversion equation is an equation for converting "the coordinates of an arbitrary point in the real space on the orthogonal coordinate axes O-xyz" into "the coordinates of the point resulting from the first mapping in the voxel space on the orthogonal coordinate axes O'-x'y'z'".

For example, as shown in FIG. 20, it is assumed that the point resulting from the first mapping of the position of the image position/orientation detection coil 44, that is, the center of the radial scan and the center O" of the ultrasound tomographic image is a mapping radial scanning surface center C'. In addition, it is assumed that the position vector of the mapping radial scanning surface center C' on the orthogonal coordinate axes O'-x'y'z' is OC'. In this case, if the first conversion equation is used, the position vector OO" of the point O" on the orthogonal coordinate axes O-xyz is converted into the coordinates O'C' of the mapping radial scanning surface center C' on the orthogonal coordinate axes O'-x'y'z'.

However, in the present embodiment, the positions of the body surface feature points A1, A2, A3, and A4 on the subject 100 which are obtained in the real space and the position O" and the orientation of the ultrasound tomographic image are obtained at different times. Therefore, there is a possibility that the subject 100 moves while the positions and orientations are obtained.

Therefore, in the present embodiment, the variation of the posture of the subject 100 is corrected based on the respective body surface feature points A1, A2, A3, and A4, and information on the position and the orientation of the posture detection coil 43 obtained almost simultaneously with the position O" and all the orientations of the ultrasound tomographic image. For example, the position vectors $OA1(t)$, $OA2(t)$, $OA3(t)$, and $OA4(t)$ of the respective body surface feature points A1, A2, A3, and A4 at the time t when the center O" of the ultrasound tomographic image was obtained are estimated from the position vector $OS(t)$ of the posture detection coil 43 and unit vectors $W(t)$, $W3(t)$, and $W12(t)$ indicating the orientation thereof at the time t when the center O" of the ultrasound tomogrpahic image was obtained. The method is shown below.

The position of the posture detection coil 43 at the time t1 when the position vector OA1 of the xiphoid process was obtained is $OS(t1)$ and the orientation is $W(t1)$, $W3(t1)$, and $W12(t1)$, so that the position vector OA1 of the xihpoid process is expressed by the following equation.

$$OA1=OS(t1)+a1\times W(t1)+b1\times W3(t1)+c1\times W12(t1)$$

Based on the equation, a1, b1, and c1 are calculated as constant numbers (scalar amounts). Here, the relative position of the xiphoid process position A1 with respect to the posture detection coil 43 is assumed to be substantially constant, and the position vector $OA1(t)$ of the xiphoid process at the time t is estimated as the following equation.

$$OA1(t)=OS(t)+a1\times W(t)+b1\times W3(t)+c1\times W12(t)$$

Similarly, also $OA2(t)$, $OA3(t)$, and $OA4(t)$ are estimated.

In the present embodiment, by using the position vectors of the body surface feature points at the time t, $OAI(t)$, $OA2(t)$, $OA3(t)$, and $OA4(t)$, the oblique coordinate system with the three vectors directed from the xiphoid process to the other points as fundamental vectors is defined, and the first conversion equation at the time t is created. That is, the first conversion equation is changed as needed depending on the variation of the position and orientation of the posture detection coil 43, that is, the variation of the posture of the subject 100. The change of the first conversion equation depending on the variation of the posture of the subject 100 is performed in synchronization with a detection cycle of the position O" and the orientation of the ultrasound tomographic image.

After the calculation of the first conversion equation in the step S51, the control circuit 60 instructs the matching circuit 61 to obtain the first mapping in which the in-vivo feature points P, Q, and R in the real space (orthogonal coordinate axes O-xyz) is mapped in the voxel space (orthogonal coordinate axes O'-x'y'z') (step S52). Here, the mapping points of the in-vivo feature points P, Q, and R in the voxel space, which are obtained using the first conversion equation, are assumed to be mapping in-vivo feature points P', Q', and R', respectively.

The calculation method of the mapping in-vivo feature points P', Q', and R' is described in detail. If times when the in-vivo feature points P, Q, R were obtained are tp, tq, and tr, respectively, the third data group obtained in the step S02 is expressed as $OO"(tp)$, $V(tp)$, $V3(tp)$, $V12(tp)$, $OO"(tq)$, $V(tq)$, $V3(tq)$, $V12(tq)$, $OO"(tr)$, $V(tr)$, $V3(tr)$, $V12(tr)$.

By using these, the position vector OP of the in-vivo feature point P can be expressed as follows.

$$OP=OO"(tp)+e\times V(tp)+f\times V3(tp)+g\times V12(tp)$$

Here, e, f, and g are known constant numbers decided by the positional relationship (design value) between the optical observation window 24 and the image position/orientation detection coil 44. Similarly, the position vector OQ of the in-vivo feature point Q and the position vector OR of the in-vivo feature point R are calculated.

The position vectors O'P', O'Q', and O'R' of the respective mapping in-vivo feature points P', Q', and R' are calculated by mapping the position vectors OP, OQ, and OR of the respective in-vivo feature points P, Q, and R on the orthogonal coordinate axes O-xyz onto the orthogonal coordinate axes O'-x'y'z' respectively using the first conversion equation at the time tp, tq, and tr.

Next, the control circuit 60 causes the matching circuit 61 to store the position vectors O'P', OQ', and O'R' of the mapping in-vivo feature points P', Q', and R' in the voxel space (orthogonal coordinate axes O'-x'y'z') (step S53).

Figure 17:
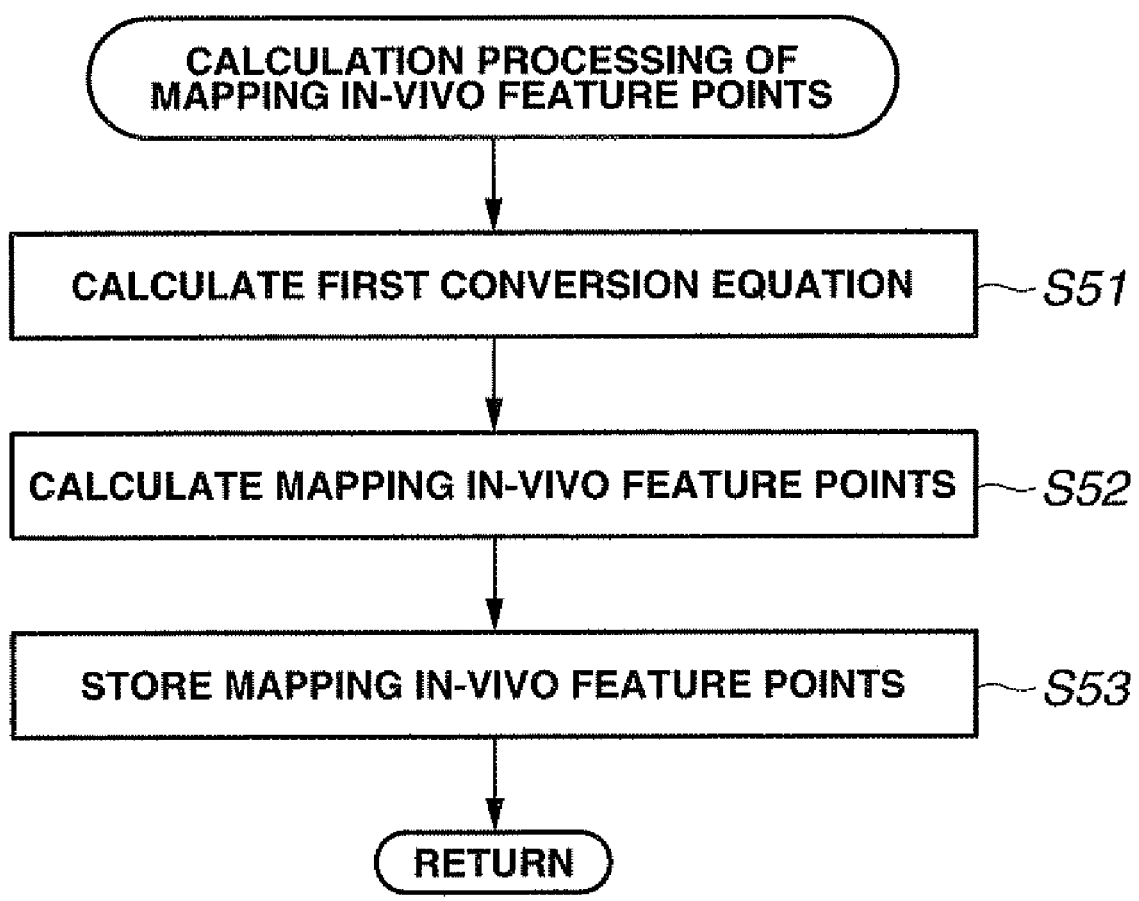
FIG. 17 is a flowchart of a mapping in-vivo feature point calculation processing.

In the processing shown in the flowchart in FIG. 17, the first conversion equation is calculated from the fourth and the fifth data groups previously obtained in the step S01, and the first, the second, and the third data groups obtained in step S02, and the mapping in-vivo feature points P', Q', and R' as the first mapping of the in-vivo feature points P, Q, and R in the real space (orthogonal coordinate axes O-xyz) are obtained by using the first conversion equation by the medical guiding system 1. Then, the procedure returns to the main routine shown in the flowchart in FIG. 14.

Figure 18:
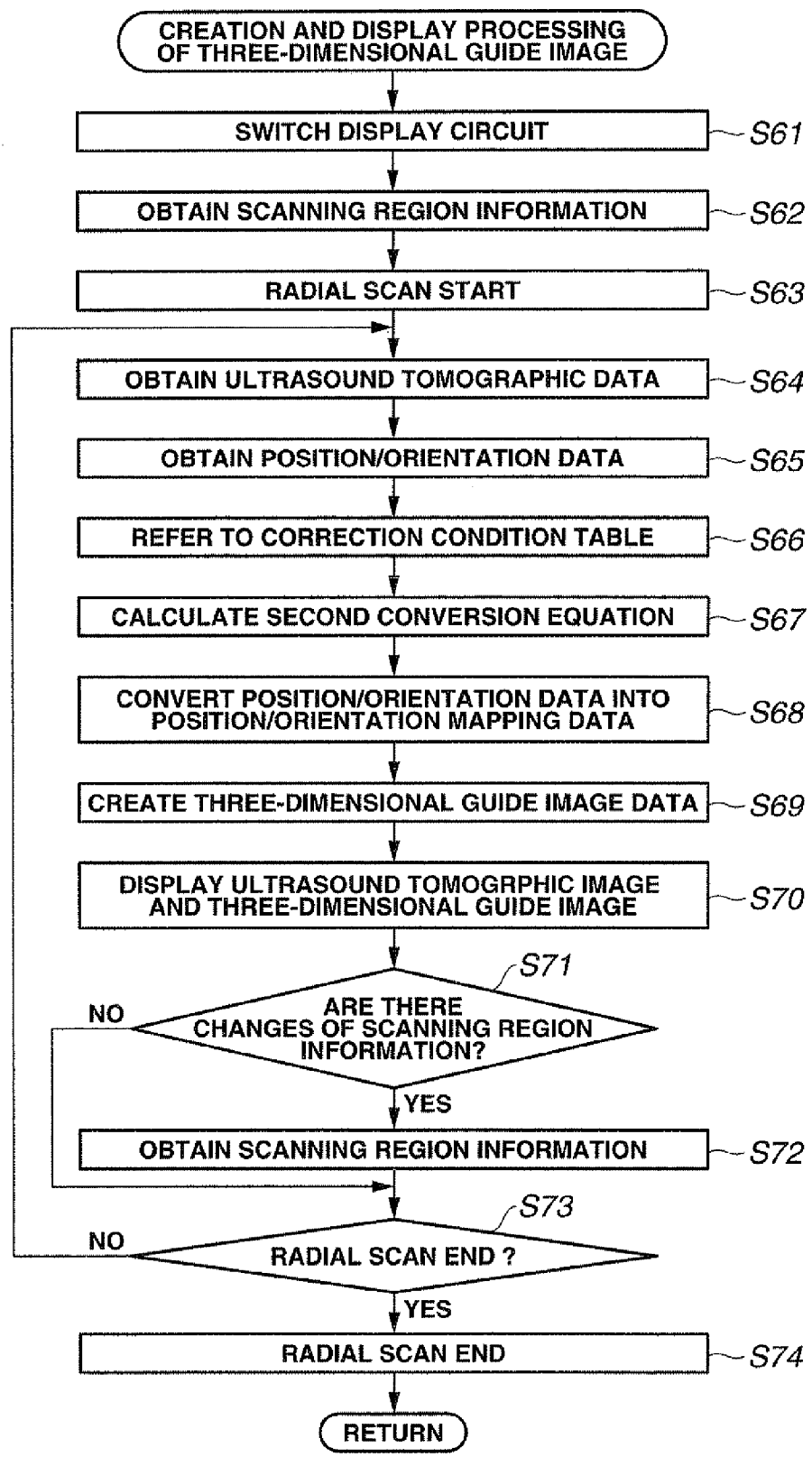
FIG. 18 is a flowchart of a three-dimensional guide image creation and display processing.

Next, description is made below, with reference to the flowchart in FIG. 18, on the details of the creation and display processing of the three-dimensional guide image in the step S05 in the flowchart shown in FIG. 14. Note that, description is made below taking as an example a case where the region to be scanned by the ultrasound endoscope 2 is a duodenal bulb, for the convenience of the description.

First, depressing the display switching key 12γ on the keyboard 12 by the operator causes the control circuit 60 to switch the switch 69 of the display circuit 68 to the input terminal 69γ (step S61). This allows the mixing data outputted from the mixing circuit 67 to be displayed on the screen of the display apparatus 8, as shown in FIG. 13.

Next, the control circuit 60 displays the list of the scanning regions described on the correction condition table 102 shown in FIG. 7, and performs a display to prompt the operator to select from the list the region to be scanned from now by the ultrasound endoscope 2. Then, the control circuit 60 stores the name of the scanning region selected by the operator depressing the scanning region selection key 12g on the keyboard 12, as the scanning region information (step S62). In the present embodiment, the scanning region described on the correction condition table 102 are three regions, that is, the stomach, the duodenal bulb, and the duodenal descending limb, and the duodenal bulb is selected by the operator.

Next, depressing the scan control key 12d on the keyboard 12 by the operator causes the control circuit 60 to output a scan control signal to the ultrasound observation apparatus 3, and to cause the ultrasound transducer array 31 to start radial scan (step S63).

Next, the control circuit 60 instructs the mixing circuit 67 to obtain the ultrasound tomographic image data outputted from the ultrasound observation apparatus 3 (step S64).

Next, the matching circuit 61 obtains and stores the position/orientation data outputted from the position/orientation calculation apparatus 4 (step S65). Note that, the position/orientation data is obtained in the step S65 in synchronization with the timing that the mixing circuit 67 obtains the ultrasound tomographic image data in the step S63.

The position/orientation data obtained in the step S65 includes the information on the positions and the orientations of the image position/orientation detection coil 44 and the posture detection coil 43 on the orthogonal coordinate axes O-xyz. That is, the position/orientation data obtained in the step S65 includes the information on the position vector OO" of the center O" of the ultrasound tomographic image, the unit vectors V, V3, and V12 indicating the orientation of the ultrasound tomographic image, and the position vector OS of the posture detection coil 43, and the unit vectors W, W3, and W12 indicating the orientation thereof.

Next, the matching circuit 61 refers to, from the correction condition table 102, the information on presence or absence of the correction execution and the correction feature points to be used for each correction, which corresponds to the stored scanning region information (step S66).

The correction here, though details thereof will be described later, is to eliminate the deviation between "the anatomical position and orientation of the image position/orientation detection coil 44 in the real subject 100" and "the anatomical position and orientation of the image position/orientation detection coil 44 in the voxel space after the mapping" which occurs in mapping the position and the orientation of the image position/orientation detection coil 44 in the real space that are obtained in the step S65 into the voxel space. In other words, the correction is to eliminate the deviation between the position and orientation of the radial scanning surface with respect to the scanning region inside the body of the subject 100 and the anatomical position and orientation of the ultrasound tomographic image marker 121 in the three-dimensional guide image data 82 shown in FIG. 13.

In the present embodiment, as shown in FIG. 7, two kinds of correction methods, that is, translation correction and scale size correction are defined. In the present embodiment, the scanning region information is that related to the duodenal bulb, so that the line of the duodenal bulb on the correction condition table 102 is referred to as a parameter of the scanning region in the step S66. That is, the presence or absence of the execution of translation correction is the presence (ON) and the translation correction feature point D as the feature point used for the translation correction is the pylorus. In addition, the presence or absence of execution of the scale size correction is the presence (ON) and a first scale size correction feature point E and a second scale size correction feature point F as the two feature points used for scale size correction are the duodenal papilla and the cardia, respectively.

Next, the matching circuit 61 uses, among the position/orientation data obtained in the step S65, the position vector OS(t) of the posture detection coil 43 and the unit vectors W(t), W3(t), and W12(t) indicating the orientation thereof, to calculate and estimate the position vectors OA1(t), OA2(t), OA3(t), and OA4(t) of the respective body surface feature points A1, A2, A3, and A4 at the time t when the position/orientation data has been obtained. Then the matching circuit 61 uses the newly calculated position vectors OA1(t), OA2(t), OA3(t) and OA4(t) to calculate the first conversion equation at the time t similarly in the step S04, and updates the first conversion equation stored in the step S04.

Then, the matching circuit 61 adds the correction determined to be executed in the step S66 to the updated first conversion equation, to newly create the second conversion equation expressing the second mapping (step S67).

Here, the second mapping means a state where the correction defined on the correction condition table 102 is executed with respect to the first mapping based on the above-described first conversion equation, in which the position and orientation of the image position/orientation detection coil 44 in the real space (orthogonal coordinate axes O-xyz) are mapped into the voxel space (orthogonal coordinate axes O'-x'y'z).

Moreover, the translation correction is to translate the entirety of the first mapping in the voxel space such that, defining one point among the reference image in-vivo feature points P", Q", and R" as the translation correction feature point D, one point of the mapping in-vivo feature points P', Q', and R' as the first mapping of the in-vivo feature points P, Q, and R of the subject 100 (hereinafter, this point is referred to as the point D'), which corresponds to the translation correction feature point D, coincides with the translation correction feature point D.

Furthermore, the scale size correction is as follows. First, two points among the reference image in-vivo feature points P", Q", and R" are defined as a first scale size correction feature point E and a second scale size correction feature point F, and a vector from the first scale size correction feature point E to the second scale size correction feature point F is defined as a reference vector EF. Then, the two points corresponding to the first scale size correction feature point E and the second scale size correction feature point F among the mapping in-vivo feature points P', Q', and R' as the first mapping of the in-vivo feature points P, Q, and R of the subject 100 are defined as a point E' and a point F', respectively, and a vector from the point E' to the point F' is defined as a mapping reference vector E'F'.

Then the ratio of scalar amounts for the respective directional components of the three axes (x' axis, y' axis, and z' axis) of the mapping reference vector E'F' with respect to the reference vector EF is calculated, and the ratio of the scalar amounts for the three axes directions is defined as a scale size correction value G. That is, when the directional components of the x' axis, the y' axis, and the z' axis of the reference vector EF are defined as e1, e2, and e3, respectively, and the directional components of the x' axis, y' axis, and z' axis of the mapping reference vector E'F' are defined as e1', e2', and e3', the scale size correction value G is a set of three scalar amounts expressed as follows.

$$Gx' = e1/e1'$$

$$Gy' = e2/e2'$$

$$Gz' = e3/e3'$$

On the other hand, the vector from the point D' set at the time of the above-described translation correction to the mapping radial scanning surface center C' as the first mapping of the position O" of the image position/orientation detection coil 44 is defined as a vector D'C'.

Then, the vector as a result of multiplying the scalar amounts of the vector D'C' of the directional components of three axes (x' axis, y' axis, and z' axis) by the scale size correction value G (Gx', Gy', Gz') is defined as a correction vector D'C".

That is, when the directional components of the X' axis, the y' axis, and the z' axis of the vector D'C' are defined as d1, d2, and d3, respectively, and the vector D'C' is described as vector D'C'=(d1·i'd2·j'd3·k'), the correction vector D'C" is expressed as follows.

The correction vector D'C"=(Gx'·d1·i'Gy'·d2·j'Gz'·d3·k).

Then, the position vector OC" is calculated by figuring out the sum of the position vector O'D of the above-described translation correction feature point D and the correction vector D'C". The point C" in the voxel space (orthogonal coordinate axes O'-x'y'z') expressed by the position vector OC" is assumed to be the position of the image position/orientation detection coil 44 after the scale size correction. That is, the point C" is the second mapping of the position of the image position/orientation detection coil 44 in the real space (orthogonal coordinate axes O-xyz).

Figure 21:
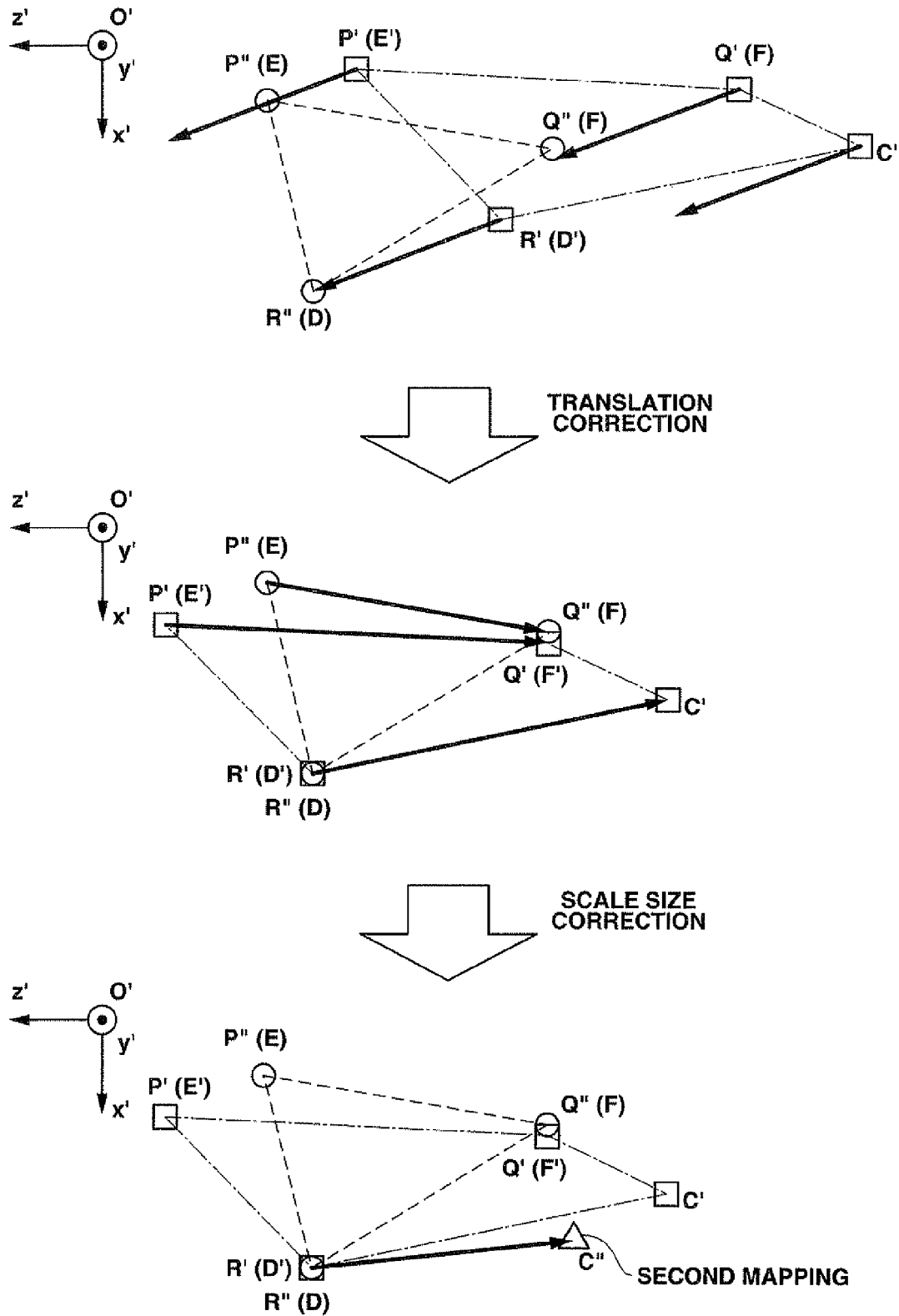
FIG. 21 is a diagram for schematically describing a method of figuring out a second mapping in the voxel space.

Hereinafter the second mapping according to the present embodiment is specifically described with reference to FIG. 21. FIG. 21 is a view schematically describing the method of figuring out the second mapping in the voxel space (orthogonal coordinate axes O'-x'y'z').

The upper part of FIG. 21 shows the positional relationship between the first mapping obtained using the first conversion equation and the reference image in-vivo feature points P", Q", and R". In the upper part of FIG. 21, the three reference image in-vivo feature points P", Q", and R" obtained in the step S01 are shown by outlined circle marks. Furthermore, the mapping in-vivo feature points P', Q', and R' and the mapping radial scanning surface center C' as the first mapping obtained in the step S04 are shown by outlined square marks.

Here, the translation correction feature point D is the pylorus (R"). Therefore, the entirety of the mapping in-vivo feature points P', Q', and R' and the mapping radial scanning surface center C' as the first mapping are translated such that the point R' corresponding to the pylorus among the mapping in-vivo feature points P', Q', and R' coincides with the translation correction feature point D in the voxel space. The middle part of FIG. 21 shows a state where the translation correction has been executed with respect to the voxel space shown in the upper part of FIG. 21.

Next, the first scale size correction feature point E and the second scale size feature point F as the two feature points used in the scale size correction are the duodenal papilla (P") and the cardia (Q"). Therefore, the reference vector EF is the vector from the duodenal papilla (P") to the cardia (Q"), and the mapping reference vector E'F' is the vector from the duodenal papilla (P') to the cardia (Q') in the first mapping.

Next, the scale size correction value G is calculated from the ratio of the directional components of the three axes of the reference vector EF and the mapping reference vector E° F', to find the correction vector D'C" by multiplying the vector D'C' in the first mapping by the scale size correction value G.

Next, the sum of the correction vector D'C" and the position vector O'D of the translation correction feature point D are figured out, and the positional coordinates of the point C" are obtained as the position of the image position/orientation detection coil 44 after the scale size correction. The lower part of FIG. 21 shows a state after the scale size correction has been executed with respect to the voxel space shown in the middle part of FIG. 21, that is, the second mapping.

In the present embodiment, the second mapping is thus figured out from the first mapping, and the conversion equation to obtain the second mapping from the first mapping is the second conversion equation created in the step S67.

Next, the matching circuit 61 converts, among the position/orientation data obtained in the step S65, the position vector OO" of the center O" of the ultrasound tomographic image in the real space (orthogonal coordinate axes O-xyz) and the unit vectors V, V3, and V12 indicating the orientation of the image position/orientation detection coil with respect to the orthogonal coordinate axes O-xyz into the position/orientation mapping data, using the first and second conversion equations (step S68).

As shown in FIG. 21, the center O" of the ultrasound tomographic image is mapped to the point C' in the voxel space using the first equation, and the center C' of the ultrasound tomographic image is mapped to the point C" in the voxel space by using the second conversion equation, as shown in FIG. 21.

Next the image index creation circuit 62 creates image index data based on the position/orientation mapping data created by the matching circuit 61. Then, the synthesis circuit 63 synthesizes the three-dimensional human body image data and the image index data, to create synthetic three-dimensional data. Then, the rotational transformation circuit 64 executes rotation processing on the synthetic three-dimensional data.

Next, each of the three-dimensional guide image creation circuits A65 and B66 creates three-dimensional guide image data (step S69).

Then, the mixing circuit 67 creates mixing data for adjacently displaying the ultrasound tomographic image data and the three-dimensional guide image data. The display circuit 68 converts the mixing data into an analog video signal. Based on this analog video signal, the display apparatus 8 adjacently displays the ultrasound tomographic image, the three-dimensional guide image of when the subject 100 is observed from the ventral side, and the three-dimensional guide image in which the normal line of the ultrasound tomographic image marker is coincided with that of the screen as shown in FIG. 13 (step S70).

Next, the control circuit 60 determines whether or not the scanning region information has been changed by the operator's depression of the scanning region selection key 12*g* (step S71). Here, when determining that the scanning region has been changed in response to the instruction by the operator, the control circuit 60 moves on to the step S72 and obtains new scanning region information, and then moves on to the step S73. On the other hand, when determining that the scanning region has not been changed, the control circuit 60 skips the step S72 and moves on to the step S73.

Next, the control circuit 60 determines whether or not the scan control key 1 2*d* has been depressed by the operator during the steps S64 to S72. When determining that the scan control key 12*d* has been depressed by the operator, the control circuit 60 moves on to step S74, and after the radial scan by the ultrasound transducer array 31 is terminated, moves on to the main routine.

On the other hand, when determining that the scan control key 12*d* has not been depressed by the operator, the control circuit 60 moves on to the step S64 to repeat the processings of the step S64 and onward. Thus, by repeating the processings from the steps S64 through S73, every time the ultrasound observation apparatus 3 creates the ultrasound tomographic image data by one radial scan by the ultrasound transducer array 31 and the created ultrasound tomographic image data is inputted from the ultrasound observation apparatus 3 to the mixing circuit 67, a new three-dimensional guide image data is created and the three-dimensional guide image to be displayed on the display apparatus 8 is updated in real time.

That is, as shown in FIG. 13, in conjunction with the resultant movement of the radial scanning surface of the manual operation of the flexible portion 22 and rigid portion 21 by the operator, the ultrasound tomographic image marker 121, the distal direction marker 122, and the six o'clock direction marker 123 on the image index data moves or deforms on the three-dimensional human body image data.

Thus, by using the medical guiding system 1 according to the present embodiment, it is possible for the operator to recognize the correspondence of the position where he or she is now observing on the ultrasound tomographic image to which anatomical position of the subject 100, on the three-dimensional guide image in which each organ is displayed in a different color, for example, while operating the ultrasound endoscope 2.

The medical guiding system 1 according to the present embodiment thus configured creates a guide image displaying the position and orientation of the ultrasound endoscope 2 as a medical instrument in real time on the reference image data obtained in advance, and especially repeats the processings described in the steps S64 to S68, and, after converting the position/orientation data at the moment that the mixing circuit 67 loads the ultrasound tomographic image data into the first mapping by using the first conversion equation, newly creates the second conversion equation expressing the second mapping in which the translation correction and the scale size correction are combined, to convert the position vector OO" of the center O" of the ultrasound tomographic image on the orthogonal coordinate axes O-xyz and unit vectors V, V3, and V12 indicating the orientation of the image position/orientation detection coil 44 into position/orientation mapping data.

The translation correction has an effect shown below. In the present embodiment, the first mapping is defined the mapping from the subject 100 to the voxel space such that "the coordinates of an arbitrary point on the orthogonal coordinate axes O-xyz, which are expressed by the oblique coordinate system on the subject 100" are the same as "the coordinates of a point resulting from the mapping of the arbitrary point on the orthogonal coordinate axes O'-x'y'z', which are expressed by the oblique coordinate system in the voxel space".

Ideally, it is preferable that the mapping in-vivo feature point R' as the first mapping of the in-vivo feature point R into a voxel space and the reference image in-vivo feature point R" specified in the step S01 coincide with each other. However, in reality, it is difficult to accurately coincide these points with each other.

The reason is that "the spatial positional relationship between an arbitrary point on the orthogonal coordinate axes O-xyz and the oblique coordinate system on the subject 100" and "the spatial positional relationship between the point on the orthogonal coordinate axes O'-x'y'z' anatomically corresponding to the arbitrary point and the oblique coordinate system in the voxel space" do not completely coincide with each other due to various factors. If description is made using the present embodiment, though the first mapping is obtained from the respective coordinates of the body surface feature points which are characteristic points on the skeleton, the pylorus (R) as the in-vivo feature point does not always have the same positional relationship with respect to the body surface feature points on the skeleton.

The cause of this is as described in the section of the description of the related art. For example, when the group of reference image data GRD is obtained using the X-ray three-dimensional helical CT apparatus 16 or the three-dimensional MRI apparatus 15, images are normally picked up in the supine position, so that the body position is different from that in the ultrasound endoscopy performed in the left lateral position. Therefore, various organs in the subject 100 are displaced according to the gravitational force.

Accordingly, in the medical guiding system 1 of the present embodiment, by performing the above-described translation correction, the position O" of the image position/orientation detection coil 44 in the ultrasound endoscope positioned in the vicinity of the position of the in-vivo feature point and the mapping point C" of the position O" can be anatomically coincided with each other with higher accuracy.

Furthermore, the scale size correction has an effect shown below. When only the translation correction is performed with respect to the first mapping (the scale size correction is not performed), the translation correction feature point D (the in-vivo feature point R in the present embodiment) used in the translation correction coincides with the position in the real space. However, the more distant from the translation correction feature point D the scanning region is, the more difficult it becomes to make the position O" of the image position/orientation detection coil 44 coincide with the mapping point C".

The reason is that "the spatial positional relationship between an arbitrary point on the orthogonal coordinate axes O-xyz and the oblique coordinate system on the subject 100" and "the spatial positional relationship between the point on the orthogonal coordinate axes O'-x'y'z' anatomically corresponding to the arbitrary point and the oblique coordinate system in the voxel space" do not completely coincide with each other due to various factors. If description is made using the present embodiment, though the first mapping is obtained from the respective coordinates of the body surface feature points which are characteristic points on the skeleton and the translation correction is performed using the pylorus (R), the distance between the position of the image position/orientation detection coil 44 positioned in the vicinity of the gallbladder on the ultrasound image and the pylorus does not necessarily correlate with the distance among the respective body surface feature points on the skeleton, for example.

The cause of this is as described in the section of the description of the related art. For example, when the group of reference image data GRD is obtained using the X-ray three-dimensional helical CT apparatus 16 or the three-dimensional MRI apparatus 15, images are normally picked up in the supine position, so that the body position is different from that in the ultrasound endoscopy performed in the left lateral position. In the left lateral position, the spine is more likely to curve than in the supine position, the positional relationship between the xiphoid process and the other three body surface feature points tends to vary (vary in scale size).

On the other hand, the viscera, the pancreas located in the retroperitoneal space in particular, are positioned on the spine side at the time of the ultrasound endoscopy, so that the viscera do not largely vary in scale size as the skeleton even if the spine is curved. On the contrary, when images are photographed using the X-ray three-dimensional helical CT apparatus or the three-dimensional MRI apparatus, the subject is in a deep inspiration state, so that the diaphragm drops to compress the viscera, and the distance among the viscera tends to be shorter.

Accordingly, in the medical guiding system I of the present embodiment, the scale size correction is performed such that the distance between the two in-vivo feature points on the reference image and that on the subject are coincided with each other to obtain the second mapping. Therefore, the position O" of the image position/orientation detection coil 44 and the mapping point C" thereof at the position away from the translation correction feature point D (in-vivo feature point R in the present embodiment) can be anatomically coincided with each other with higher accuracy.

As described above, the medical guiding system 1 according to the present embodiment has an effect that the position of the ultrasound endoscope as a medical instrument on the guide image can be coincided with the real position in the body of the subject with high accuracy, even in a case where the scale sizes of the body surface feature points (the skeleton) and the in-vivo feature points (the viscera) in the body position of the subject at the time ultrasound endoscopy are different from those in the body position of the human body at the time that the reference image data has been obtained.

In addition, when the human body from which the group of reference image data GRD has been obtained and the subject of the ultrasound endoscopy are of different persons, the scale size of the viscera with respect to the skeleton is different due to personal difference. However, with the medical guiding system 1 according to the present embodiment, the matching circuit 61 creates, after the conversion into the first mapping using the first conversion equation, the second conversion equation expressing the second mapping by combining the translation correction and the scale size correction. Therefore, even if the scale size of the viscera with respect to the skeleton on the reference image data is different from that on the subject, the position of the ultrasound endoscope on the guide image can be coincided with the real position in the body of the subject.

In addition, with the present embodiment, in a case where the scanning region is changed, when the operator depresses the scanning region selection key 12g to select the scanning region from the three regions, that is, the stomach, the duodenal bulb, and the duodenal descending limb, the matching circuit 61, based on the stored correction condition table 102, decides feature points to be used in each correction depending on the selected scanning region. Therefore, the translation correction and the scale size correction can be performed using the feature point near the scanning region, thereby enabling the ultrasound tomographic image to be guided more accurately using the three-dimensional guide image.

In addition, with the present embodiment, in a case where the scanning region is changed, when the operator depresses the scanning region selection key 12g to select the scanning region from three regions, that is, the stomach, the duodenal bulb, and the duodenal descending limb, the matching circuit 61, based on the stored correction condition table 102, decides the presence or the absence of each correction and the feature point to be used in each correction depending on the scanning region. Accordingly, even if the diaphragm of the subject drops to compress the viscera in the body axis direction (head and foot direction) and the scale size of the viscera with respect to the skeleton varies at the time of photographing an image using the X-ray three-dimensional helical CT apparatus 16 and the three-dimensional MRI apparatus 15, compared with the ultrasound endoscopy in the normal respiratory state, the presence or absence of execution of the scale size correction is switched in accordance with the compression rate of the respective regions of the viscera, and optimum feature point can be selected, thereby enabling the ultrasound tomographic image to be more accurately guided using the three-dimensional guide image.

Note that, though the positions of the in-vivo feature points are obtained by bringing the observation window of the ultrasound endoscope into contact with the in-vivo feature points in the above-described present embodiment, the configuration is not limited to this. Alternatively, an ultrasound endoscope including a forceps channel and an in-vivo contact probe to be inserted through the forceps channel are provided, and the positions of the in-vivo feature points may be obtained by bringing the distal end of the in-vivo contact probe into contact with the in-vivo feature points. In addition, the in-vivo feature points may be obtained by selecting the in-vivo feature points on an ultrasound image or on an optical image.

In addition, in the present embodiment, an electronic radial scan ultrasound endoscope is used as an ultrasound probe in the present embodiment. However, as other known ultrasound diagnostic apparatuses, a mechanical scan ultrasound endoscope, an electronic convex scan ultrasound endoscope including a group of ultrasound transducers provided in a fan shape at one side of the insertion axis, or capsule ultrasound sonde may be used, and there is no limitation placed on the ultrasound scanning method. Furthermore, an ultrasound probe without the optical observation window may be used.

Furthermore, in the present embodiment, in the rigid portion of the ultrasound endoscope, the ultrasound transducers cut into small pieces like strips are arranged around the insertion axis as an annular array, however, the ultrasound transducer array may be provided all around the circumference of the insertion axis through 360 degrees or may be provided around the circumference through less than 360 degrees, for example, through 270 degrees or 180 degrees.

In addition, in the present embodiment, the ultrasound endoscope is used as the medical instrument, however, the medical instrument may be a bronchoscope, gastrointestinal endoscope, a laparoscope, and the like. Furthermore, the medical instrument is not limited to the endoscope, but may be a so-called extracorporeal ultrasound diagnostic apparatus, which employs a method of irradiating ultrasound from outside the body.

In addition, in the present embodiment, the transmission antenna and the reception coil are used as position detection means to detect the position and orientation based on the magnetic field, however the transmission and reception relationship may be reversed, and the position and orientation may be detected using acceleration or other means instead of the magnetic field.

In addition, in the present embodiment, the origin O is set at a specific position on the transmission antenna. However, the origin O may be set in another position having the same positional relationship with respect to the transmission antenna.

In addition, the image position/orientation detection coil is fixedly provided to the rigid portion in the present embodiment. However, the image position/orientation detection coil need not necessarily be disposed inside of the rigid portion, as far as the position of the image position/orientation detection coil with respect to the rigid portion is fixed.

In addition, in the present embodiment, the organs on the three-dimensional guide image data are displayed in different colors by each organ. However, the present invention is not limited to the use of the variation in display color but may use another aspect such as luminance, brightness, color saturation, or the like.

Moreover, in the present embodiment, a plurality of two-dimensional CT images or the two-dimensional MRI images picked up by the X-ray three-dimensional helical CT apparatus or the three-dimensional MRI apparatus are used as the reference image data. However, three-dimensional image data previously obtained using another modality such as PET (Positron Emission Tomography) may be used. Alternatively, the three-dimensional image data previously obtained by a so-called extracorporeal ultrasound diagnostic apparatus, which employs a method of irradiating ultrasound from outside the body, may be used.

Furthermore, the reference image data may be obtained from the subject himself or herself, or the image data previously obtained from other person of the same sex and similar body size may be used.

Though the posture detection coil is fixed to the body surface of the subject to obtain position/orientation data in the present embodiment, a body surface detection coil composed of four coils wound in one axis direction is provided, and the coils may be detachably fixed to a plurality of body surface feature points on the subject's body surface with a tape, a belt, a band or the like, to simultaneously obtain position/orientation data of the body surface feature points. With such a configuration, guide images can be accurately created, even when the posture of the subject has varied at the time of using the medical guiding system 1 and the positional relationship among the four body surface feature points has varied.

In addition, instead of using the posture detection coil, it may be configured such that the body surface detection coil is brought into contact sequentially with the plurality of body surface feature points only once in advance, to sequentially obtain the position/orientation data of the body surface feature points.

(Second Embodiment)

The second embodiment of the present invention is described below. The present embodiment differs from the first embodiment only in the method of performing the scale size correction, but the configurations of the apparatuses are the same. Therefore, only the different point is described below.

In the medical guiding system 1 of the present embodiment, the scale size correction to be executed in the step S68 is performed only using a component Gz' in the body axis direction (z' axis direction) of the subject 100 among the scale correction values G.

Here, the curve of the spine of the subject 100 and the direction in which the viscera are compressed by respiration are mainly the body axis direction. Therefore, with the present embodiment, the calculation amount required for the scale size correction can be decreased compared with the first embodiment, thereby enabling the guide image to be displayed with high real time property.

In addition, the three in-vivo feature points P, Q, and R can be obtained in a wide range in the body axis direction, but can not be obtained in a wide range in the direction perpendicular to the body axis (x' axis direction, y' axis direction). Therefore, as for the direction orthogonal to the body axis, the error at the time of obtaining the in-vivo feature points has a great influence on the correction accuracy. As a result, there is a possibility that the coincidence degree between the three-dimensional guide image and the ultrasound tomographic image is reduced. However, with the present embodiment, the scale size correction is not executed in the direction perpendicular to the body axis (x' axis direction and y' axis direction), thereby enabling a more accurate three-dimensional guide image to be displayed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical guiding system comprising:
a detection portion configured to detect at least one of a position and an orientation of a medical instrument and at least one of positions and orientations of a plurality of feature points of a subject in a real space;
a storage portion configured to store reference image data having anatomical positional information on at least one organ of a human body; and
a guide image creation portion configured:
to define a mapping for converting at least one of the position and the orientation of the medical instrument in the real space into at least one of a position and an orientation in the reference image data based on information on:
at least one of positions and orientations of the plurality of feature points of the subject in the real space, and
at least one of positions and orientations of a plurality of reference image feature points which correspond to the plurality of feature points in the reference image data, and
to create a guide image indicating a position of the medical instrument or an observation position by the medical instrument based on the mapping and the reference image data,
to correct the position of the medical instrument or the observation position by the medical instrument which the guide image indicates, based on information on:
at least one of positions and orientations of a plurality of in-vivo feature points in a body of the subject in the real space, and
at least one of positions and orientations of one or more correction feature points which anatomically correspond to the in-vivo feature points in the reference image data, and
to change anatomical positions of the in-vivo feature points to be used in the correction depending on an anatomical region for which the medical instrument is used.

2. The medical guiding system according to claim 1, wherein
the in-vivo feature points are two, and
the correction corrects the calculated position of the medical instrument or the calculated observation position by the medical instrument by correcting a scale size of the mapping based on comparison of a distance between the two in-vivo feature points and a distance between two correction feature points.

3. The medical guiding system according to claim 2, wherein the correction moves the position of the medical instrument or the observation position by the medical instrument which the guide image indicates, such that one of the in-vivo feature points coincides with one of the reference image feature points which corresponds to the one of the in-vivo feature points, and correct the calculated position of the medical instrument or the observation position by the medical instrument.

4. The medical guiding system according to claim 3, wherein presence or absence of execution of the correction of the scale size of the mapping is switched depending on the anatomical region for which the medical instrument is used.

5. The medical guiding system according to claim 1, wherein the correction moves the position of the medical instrument or the observation position by the medical instrument which the guide image indicates, such that one of the in-vivo feature points coincides with one of the reference image feature points which corresponds to the one of the in-vivo feature points, and correct the calculated position of the medical instrument or the observation position by the medical instrument.

* * * * *